United States Patent
Sloat

(10) Patent No.: US 12,374,236 B2
(45) Date of Patent: Jul. 29, 2025

(54) DIALYSIS TRAINING USING DIALYSIS TREATMENT SIMULATION SYSTEM

(71) Applicant: Fresenius Medical Care Holdings, Inc., Waltham, MA (US)

(72) Inventor: Daniel Sloat, Lexington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 616 days.

(21) Appl. No.: 17/586,544

(22) Filed: Jan. 27, 2022

(65) Prior Publication Data

US 2023/0237929 A1    Jul. 27, 2023

(51) Int. Cl.
   *G09B 23/28*    (2006.01)
   *A61M 1/16*     (2006.01)
   *G09B 23/30*    (2006.01)

(52) U.S. Cl.
   CPC ........... *G09B 23/28* (2013.01); *A61M 1/1621* (2014.02); *A61M 2205/3306* (2013.01); *A61M 2205/502* (2013.01); *A61M 2205/583* (2013.01); *A61M 2230/04* (2013.01); *A61M 2230/435* (2013.01); *G09B 23/30* (2013.01); *G09B 23/303* (2013.01)

(58) Field of Classification Search
   CPC .... A61M 1/3609; A61M 1/14; A61M 1/1621; A61M 2205/3306; A61M 2205/502; A61M 2205/583; A61M 2230/04; A61M 2230/435; A61M 1/1613; G09B 23/28; G09B 23/30; G09B 23/303; G16H 10/20;

(Continued)

(56) References Cited

U.S. PATENT DOCUMENTS 5,853,292 A    12/1998   Eggert et al.
6,193,519 B1    2/2001   Eggert et al.
(Continued)

FOREIGN PATENT DOCUMENTS

CN    204650870 U    9/2015
CN    105784406 A    7/2016
(Continued)

OTHER PUBLICATIONS

International Patent Application No. PCT/US2022/049023, Search Report (Feb. 9, 2023).

*Primary Examiner* — Jack Yip
(74) *Attorney, Agent, or Firm* — Leydig, Voit & Mayer, Ltd.

(57) ABSTRACT

A system and method is provided for training operators (e.g., users), including new nurses or nephrologists as well as patients or their family members, to learn the intricacies of dialysis (e.g., hemodialysis) treatment through a simulation. The simulation may afford users the ability to fail catastrophically in simulated dialysis treatment, see the consequences, learn and internalize complex algorithms, and develop the ability to think in a time pressured situation. The simulation may thereby provide a safe learning environment for experiencing decisions and consequences of these decisions when performing a dialysis treatment. In some instances, the simulation may be in a mobile application form factor to encourage more ubiquitous use on personal devices, which may provide ease of access for the dialysis training. The simulation may further include time-based simulated scenarios that increase in difficulty and complexity between levels.

19 Claims, 8 Drawing Sheets

(58) Field of Classification Search
CPC ........ G16H 20/40; G16H 40/63; G16H 40/67; G16H 50/50
See application file for complete search history.

(56) References Cited

U.S. PATENT DOCUMENTS

| | | |
|---|---|---|
| 6,386,882 B1 | 5/2002 | Linberg |
| 6,443,735 B1 | 9/2002 | Eggert et al. |
| 6,503,087 B1 | 1/2003 | Eggert et al. |
| 6,527,558 B1 | 3/2003 | Eggert et al. |
| 6,535,714 B2 | 3/2003 | Melker et al. |
| 6,758,676 B2 | 7/2004 | Eggert et al. |
| 7,114,954 B2 | 10/2006 | Eggert et al. |
| 7,192,284 B2 | 3/2007 | Eggert et al. |
| 7,464,040 B2 | 12/2008 | Joao |
| 7,490,048 B2 | 2/2009 | Joao |
| 7,811,090 B2 | 10/2010 | Eggert et al. |
| 7,976,312 B2 | 7/2011 | Eggert et al. |
| 7,976,313 B2 | 7/2011 | Eggert et al. |
| 8,016,598 B2 | 9/2011 | Eggert et al. |
| 8,152,532 B2 | 4/2012 | Eggert et al. |
| 8,346,482 B2 | 1/2013 | Fernandez |
| 8,364,411 B2 | 1/2013 | Fernandez |
| 8,364,413 B2 | 1/2013 | Fernandez |
| 8,370,068 B1 | 2/2013 | Fernandez |
| 8,370,070 B2 | 2/2013 | Fernandez |
| 8,370,071 B2 | 2/2013 | Fernandez |
| 8,370,072 B2 | 2/2013 | Fernandez |
| 8,370,073 B2 | 2/2013 | Fernandez |
| 8,370,078 B2 | 2/2013 | Fernandez |
| 8,374,796 B2 | 2/2013 | Fernandez |
| 8,419,438 B2 | 4/2013 | Eggert et al. |
| 8,423,298 B2 | 4/2013 | Fernandez |
| 8,678,832 B2 | 3/2014 | Eggert et al. |
| 8,696,362 B2 | 4/2014 | Eggert et al. |
| 8,827,708 B2 | 9/2014 | Christensen et al. |
| 8,951,047 B2 | 2/2015 | Egger et al. |
| 9,004,922 B2 | 4/2015 | Eggert et al. |
| 9,047,787 B2 | 6/2015 | Pybus et al. |
| 9,110,836 B1 | 8/2015 | Fernandez |
| 9,111,026 B1 | 8/2015 | Fernandez |
| 9,147,041 B2 | 9/2015 | Amarasingham et al. |
| 9,230,221 B2 | 1/2016 | Gobert et al. |
| 9,317,115 B2 | 4/2016 | Gobert et al. |
| 9,324,247 B2 | 4/2016 | Eggert et al. |
| 9,336,354 B1 | 5/2016 | Sankara et al. |
| 9,378,659 B2 | 6/2016 | Eggert et al. |
| 9,406,244 B2 | 8/2016 | Eggert et al. |
| 9,536,052 B2 | 1/2017 | Amarasingham et al. |
| 9,715,839 B2 | 7/2017 | Pybus et al. |
| 9,719,147 B1 | 8/2017 | Fernandez |
| 9,801,993 B2 | 10/2017 | Barrett et al. |
| 9,839,483 B2 | 12/2017 | Sankaran et al. |
| 9,870,720 B2 | 1/2018 | Eggert et al. |
| 9,993,303 B2 | 6/2018 | Sankaran et al. |
| 10,061,899 B2 | 8/2018 | Miller et al. |
| 10,068,061 B2 | 9/2018 | Miller et al. |
| 10,089,443 B2 | 10/2018 | Miller et al. |
| 10,095,840 B2 | 10/2018 | Miller et al. |
| 10,224,117 B2 | 3/2019 | Miller et al. |
| 10,285,762 B2 | 5/2019 | Sankaran et al. |
| 10,311,970 B2 | 6/2019 | Tiwari et al. |
| 10,314,654 B2 | 6/2019 | Sankaran et al. |
| 10,496,788 B2 | 12/2019 | Amarasingham et al. |
| 10,593,426 B2 | 3/2020 | Amarasingham et al. |
| 10,726,744 B2 | 7/2020 | Benson et al. |
| 10,755,369 B2 | 8/2020 | Amarasingham et al. |
| 10,758,660 B2 | 9/2020 | Leinfellner et al. |
| 10,786,308 B2 | 9/2020 | Sankaran et al. |
| 10,867,708 B2 | 12/2020 | Cock et al. |
| 10,878,936 B2 | 12/2020 | Fernandez |
| 11,031,128 B2 | 6/2021 | Plahey et al. |
| 2001/0032099 A1 | 10/2001 | Joao |
| 2002/0001794 A1 | 1/2002 | Melker et al. |
| 2002/0032583 A1 | 3/2002 | Joao |
| 2002/0132214 A1 | 9/2002 | Mattson et al. |
| 2003/0011646 A1 | 1/2003 | Levine et al. |
| 2003/0073060 A1 | 4/2003 | Eggert et al. |
| 2003/0091968 A1 | 5/2003 | Eggert et al. |
| 2004/0157199 A1 | 8/2004 | Eggert et al. |
| 2004/0214150 A1 | 10/2004 | Eggert et al. |
| 2005/0043894 A1 | 2/2005 | Fernandez |
| 2006/0040245 A1 | 2/2006 | Airola et al. |
| 2006/0178841 A1 | 8/2006 | Fernandez |
| 2006/0253259 A1 | 11/2006 | Fernandez |
| 2007/0106333 A1 | 5/2007 | Fernandez |
| 2007/0122785 A1 | 5/2007 | Eggert et al. |
| 2008/0059249 A1 | 3/2008 | Joao |
| 2008/0059250 A1 | 3/2008 | Joao |
| 2008/0077375 A1 | 3/2008 | Fernandez |
| 2008/0131855 A1 | 6/2008 | Eggert et al. |
| 2008/0138778 A1 | 6/2008 | Eggert et al. |
| 2008/0138779 A1 | 6/2008 | Eggert et al. |
| 2008/0138780 A1 | 6/2008 | Eggert et al. |
| 2008/0176210 A1 | 7/2008 | Moll et al. |
| 2009/0148822 A1 | 6/2009 | Eggert et al. |
| 2009/0198450 A1 | 8/2009 | Fernandez |
| 2009/0198451 A1 | 8/2009 | Fernandez |
| 2009/0204379 A1 | 8/2009 | Fernandez |
| 2009/0215011 A1 | 8/2009 | Christensen et al. |
| 2009/0222215 A1 | 9/2009 | Fernandez |
| 2009/0248450 A1 | 10/2009 | Fernandez |
| 2009/0253587 A1 | 10/2009 | Fernandez |
| 2009/0305214 A1 | 12/2009 | Pybus et al. |
| 2009/0313049 A1 | 12/2009 | Joao et al. |
| 2010/0010423 A1 | 1/2010 | Yu et al. |
| 2010/0010425 A1 | 1/2010 | Yu et al. |
| 2010/0042440 A1 | 2/2010 | Joao |
| 2010/0049546 A1 | 2/2010 | Neville |
| 2010/0114602 A1 | 5/2010 | Joao et al. |
| 2010/0217178 A1 | 8/2010 | Lo et al. |
| 2010/0217180 A1 | 8/2010 | Akonur et al. |
| 2010/0285082 A1 | 11/2010 | Fernandez |
| 2010/0304347 A1 | 12/2010 | Eggert et al. |
| 2011/0107253 A1 | 5/2011 | Levine et al. |
| 2011/0213625 A1 | 9/2011 | Joao |
| 2011/0257891 A1 | 10/2011 | Akonur et al. |
| 2011/0265008 A1 | 10/2011 | Levine et al. |
| 2011/0311956 A1 | 12/2011 | Eggert et al. |
| 2012/0029324 A1 | 2/2012 | Akonur et al. |
| 2012/0138533 A1* | 6/2012 | Curtis ................ A61M 1/1601 210/85 |
| 2012/0197183 A1 | 8/2012 | Yu et al. |
| 2012/0214145 A1 | 8/2012 | Eggert et al. |
| 2013/0054264 A1* | 2/2013 | Baronov ............... G16H 50/50 705/2 |
| 2013/0085775 A1 | 4/2013 | Baronov et al. |
| 2013/0191097 A1 | 7/2013 | Hocum et al. |
| 2013/0226845 A1 | 8/2013 | Gobert et al. |
| 2013/0231949 A1 | 9/2013 | Baronov et al. |
| 2013/0262357 A1 | 10/2013 | Amarasingham et al. |
| 2013/0275050 A1 | 10/2013 | Neville |
| 2013/0310726 A1 | 11/2013 | Miller et al. |
| 2013/0317753 A1 | 11/2013 | Kamen et al. |
| 2013/0317795 A1 | 11/2013 | Akonur et al. |
| 2013/0330699 A1 | 12/2013 | Eggert et al. |
| 2014/0042092 A1 | 2/2014 | Akonur et al. |
| 2014/0074509 A1 | 3/2014 | Amarasingham et al. |
| 2014/0099617 A1* | 4/2014 | Tallman, Jr. ......... G09B 23/303 434/262 |
| 2014/0127663 A1 | 5/2014 | Eggert et al. |
| 2014/0180711 A1 | 6/2014 | Kamen et al. |
| 2014/0188516 A1 | 7/2014 | Kamen et al. |
| 2014/0205981 A1* | 7/2014 | Ryder ..................... G09B 7/06 434/262 |
| 2014/0205983 A1 | 7/2014 | Eggert et al. |
| 2014/0220529 A1 | 8/2014 | Eggert et al. |
| 2014/0266983 A1 | 9/2014 | Christensen |
| 2015/0154888 A1 | 6/2015 | Eggert et al. |
| 2015/0194066 A1 | 7/2015 | Samosky et al. |
| 2015/0213202 A1 | 7/2015 | Amarasingham et al. |
| 2015/0213206 A1 | 7/2015 | Amarasingham et al. |
| 2015/0213207 A1 | 7/2015 | Amarasingham et al. |
| 2015/0213217 A1 | 7/2015 | Amarasingham et al. |

(56) References Cited

U.S. PATENT DOCUMENTS

| | | |
|---|---|---|
| 2015/0213222 A1 | 7/2015 | Amarasingham et al. |
| 2015/0213223 A1 | 7/2015 | Amarasingham et al. |
| 2015/0213224 A1 | 7/2015 | Amarasingham et al. |
| 2015/0213225 A1 | 7/2015 | Amarasingham et al. |
| 2015/0221237 A1 | 8/2015 | Eggert et al. |
| 2016/0019666 A1 | 1/2016 | Amarasingham et al. |
| 2016/0026247 A1 | 1/2016 | Gobert et al. |
| 2016/0111023 A1 | 4/2016 | Pybus et al. |
| 2016/0125161 A1 | 5/2016 | Sankaran et al. |
| 2016/0125549 A1 | 5/2016 | Joao et al. |
| 2016/0125550 A1 | 5/2016 | Joao et al. |
| 2016/0125765 A1 | 5/2016 | Meretei et al. |
| 2016/0133158 A1 | 5/2016 | Sui et al. |
| 2016/0175053 A1 | 6/2016 | Sankaran et al. |
| 2016/0217265 A1 | 7/2016 | Miller et al. |
| 2016/0220123 A1 | 8/2016 | Grady et al. |
| 2016/0220124 A1 | 8/2016 | Grady et al. |
| 2016/0235901 A1 | 8/2016 | Miller et al. |
| 2016/0239637 A1 | 8/2016 | Miller et al. |
| 2016/0314601 A1 | 10/2016 | Sankaran et al. |
| 2016/0372009 A1 | 12/2016 | Eggert et al. |
| 2017/0011175 A1 | 1/2017 | Cocks et al. |
| 2017/0011190 A1 | 1/2017 | Joao |
| 2017/0039423 A1 | 2/2017 | Cork et al. |
| 2017/0178541 A9 | 6/2017 | Pybus et al. |
| 2017/0193160 A1 | 7/2017 | Long et al. |
| 2017/0220769 A1 | 8/2017 | Miller et al. |
| 2017/0229044 A1 | 8/2017 | Benson et al. |
| 2017/0262610 A1 | 9/2017 | Azevedo |
| 2018/0068465 A1 | 3/2018 | Sankaran et al. |
| 2018/0075217 A1 | 3/2018 | Tiwari et al. |
| 2018/0137783 A1 | 5/2018 | Eggert et al. |
| 2018/0218110 A1 | 8/2018 | Hocum et al. |
| 2018/0256260 A1 | 9/2018 | Sankaran et al. |
| 2018/0344919 A1 | 12/2018 | Jones et al. |
| 2019/0018931 A1 | 1/2019 | Chamney et al. |
| 2019/0019570 A1 | 1/2019 | Fuertinger et al. |
| 2019/0027064 A1 | 1/2019 | Nelson et al. |
| 2019/0064520 A1 | 2/2019 | Christensen |
| 2019/0103173 A1 | 4/2019 | Power et al. |
| 2019/0103174 A1 | 4/2019 | Power et al. |
| 2019/0134289 A1 | 5/2019 | Pudil et al. |
| 2019/0200921 A1* | 7/2019 | Barrett ................ A61B 5/6866 |
| 2019/0231437 A1 | 8/2019 | Sankaran et al. |
| 2019/0247124 A1 | 8/2019 | Sankaran et al. |
| 2019/0251230 A1 | 8/2019 | Fernandez |
| 2019/0251354 A1 | 8/2019 | Cork et al. |
| 2019/0279524 A1 | 9/2019 | Stoyanov et al. |
| 2019/0279765 A1 | 9/2019 | Giataganas et al. |
| 2019/0287668 A1 | 9/2019 | Tiwari et al. |
| 2019/0351121 A1 | 11/2019 | Akonur et al. |
| 2019/0381233 A1* | 12/2019 | Frinak ................ A61M 5/16854 |
| 2020/0118677 A1 | 4/2020 | Giataganas et al. |
| 2020/0126632 A1 | 4/2020 | Schappacher-Tilp et al. |
| 2020/0160057 A1 | 5/2020 | Roxas et al. |
| 2020/0164131 A1 | 5/2020 | Musca et al. |
| 2020/0221990 A1 | 7/2020 | Chiofolo et al. |
| 2020/0233485 A1 | 7/2020 | Chan et al. |
| 2020/0243193 A1 | 7/2020 | Plahey et al. |
| 2020/0294676 A1 | 9/2020 | Cherif et al. |
| 2020/0320901 A1 | 10/2020 | Benson et al. |
| 2020/0383731 A1 | 12/2020 | Sankaran et al. |
| 2020/0397972 A1 | 12/2020 | Ku et al. |
| 2021/0012866 A1 | 1/2021 | Amarasingham et al. |
| 2021/0104328 A1 | 4/2021 | Baronov et al. |
| 2021/0128254 A1 | 5/2021 | Geric et al. |
| 2021/0151200 A1 | 5/2021 | Cocks et al. |
| 2021/0201699 A1 | 7/2021 | Eggert et al. |
| 2021/0228094 A1 | 7/2021 | Grady et al. |
| 2021/0295741 A1* | 9/2021 | Bluemler ........... C11D 17/0095 |
| 2021/0299339 A1 | 9/2021 | Thijssen |
| 2021/0319905 A1* | 10/2021 | Monaghan .............. G16H 50/80 |
| 2024/0074680 A1* | 3/2024 | Cherif ................ A61M 1/1613 |

FOREIGN PATENT DOCUMENTS

| | | |
|---|---|---|
| CN | 205451561 U | 8/2016 |
| CN | 207458427 U | 6/2018 |
| CN | 208126709 U | 11/2018 |
| CN | 208922601 U | 5/2019 |
| CN | 113129720 A | 7/2021 |
| JP | 2004-321357 A | 11/2004 |
| JP | 2005-114764 A | 4/2005 |
| JP | 2007-029705 A | 2/2007 |
| JP | 2010-259525 A | 11/2010 |
| JP | 2020-034833 A | 3/2020 |
| TW | 201421436 A | 6/2014 |
| WO | WO 09/088308 A2 | 7/2009 |
| WO | WO 2014/100687 A1 | 6/2014 |
| WO | WO 2014/113186 A1 | 7/2014 |
| WO | WO 2015/027286 A1 | 3/2015 |
| WO | WO 2015/187616 A1 | 12/2015 |
| WO | WO 2016/089753 A1 | 6/2016 |
| WO | WO 2016/100875 A2 | 6/2016 |
| WO | WO 2016/102571 A1 | 6/2016 |
| WO | WO 2017/043440 A1 | 3/2017 |
| WO | WO 2018/126254 A1 | 7/2018 |
| WO | WO 2018/149858 A1 | 8/2018 |
| WO | WO 2021/023574 A1 | 2/2021 |
| WO | WO 2021/115835 A1 | 6/2021 |

* cited by examiner

DIALYSIS TRAINING USING DIALYSIS TREATMENT SIMULATION SYSTEM

BACKGROUND

Learning to operate a dialysis machine and performing dialysis treatment on a patient, or on oneself, is a challenging and stressful process. In particular, balancing clinical variables (e.g., patient parameters) such as arterial pressure and venous pressure while implementing complex machine operations to perform the dialysis treatment is difficult, and failure typically results in harmful consequences. Additionally, the patient parameters may relate to each other such that when an operator adjusts a particular parameter (e.g., provide oxygen (O2) to a patient or adjust a pump speed), one or more of the patient parameters may also change. Furthermore, unexpected dialysis events may occur during the dialysis treatment, which also leads to the stress of a new operator of the dialysis machine.

SUMMARY

This summary is provided to introduce certain exemplary embodiments that are further described below. This summary is not intended to be an identification of key features or essential features of the present disclosure.

In an exemplary embodiment, the present disclosure provides a hemodialysis system comprising: a hemodialysis machine having an extracorporeal blood circuit with a blood chamber and a dialyzer, wherein the hemodialysis machine is configured to perform a hemodialysis treatment for a patient; and an optical monitoring system, comprising a sensor device configured to emit light through the blood chamber and measure optical characteristics of extracorporeal blood in the blood chamber, wherein the hemodialysis machine includes or is connected to a user input interface, a display, and one or more processors configured to: initialize a simulated dialysis treatment for a simulated dialysis patient; receive, from the one or more sensors, the user input for treating the simulated dialysis patient during the simulated dialysis treatment, wherein the user input is associated with a patient parameter, of a plurality of patient parameters, for the simulated dialysis patient; update a set of patient parameters of the plurality of patient parameters for the simulated dialysis patient based on the user input, wherein the set of patient parameters comprises the patient parameter associated with the user input and one or more additional patient parameters that are associated with the patient parameter, wherein the one or more additional patient parameters comprises a blood pressure parameter indicating a blood pressure of the simulated dialysis patient; display an indicia on the display, wherein the indicia is associated with a health of the simulated dialysis patient based on updating the set of patient parameters; and subsequent to completing the simulated dialysis treatment, display a prompt on the display indicating a result of the simulated dialysis treatment based on the health of the simulated dialysis patient.

In some instances, the one or more processors are further configured to: receive, from the one or more sensors, a second user input for treating the simulated dialysis patient during the simulated dialysis treatment, wherein the second user input is associated with a second patient parameter, of the plurality of patient parameters, for the dialysis patient, wherein the second patient parameter is different from the patient parameter; and update a second set of patient parameters of the plurality of patient parameters for the simulated dialysis patient based on the second user input, wherein the second set of patient parameters comprises the second patient parameter associated with the second user input, the blood pressure parameter, and a third patient parameter that is associated with the second patient parameter.

In some examples, initializing the simulated dialysis treatment comprises determining a plurality of dialysis event variables associated with a plurality of dialysis events, and wherein the one or more processors are further configured to: execute one or more dialysis events of the plurality of dialysis events based on comparing a result from a random number generator with one or more dialysis event variables of the plurality of dialysis event variables, and wherein updating the set of patient parameters is further based on executing the one or more dialysis events.

In another exemplary embodiment, the present disclosure provides a computing device, comprising: a user input interface; a display configured to display information associated with a simulated dialysis treatment; and one or more processors configured to: initialize a simulated dialysis treatment for a simulated dialysis patient; receive, from the one or more sensors, the user input for treating the simulated dialysis patient during the simulated dialysis treatment, wherein the user input is associated with a patient parameter, of a plurality of patient parameters, for the simulated dialysis patient; update a set of patient parameters of the plurality of patient parameters for the simulated dialysis patient based on the user input, wherein the set of patient parameters comprises the patient parameter associated with the user input and one or more additional patient parameters that are associated with the patient parameter, wherein the one or more additional patient parameters comprises a blood pressure parameter indicating a blood pressure of the simulated dialysis patient; display an indicia on the display, wherein the indicia is associated with a health of the simulated dialysis patient based on updating the set of patient parameters; and subsequent to completing the simulated dialysis treatment, display a prompt on the display indicating a result of the simulated dialysis treatment based on the health of the simulated dialysis patient.

In some instances, the one or more processors are further configured to: receive, from the one or more sensors, a second user input for treating the simulated dialysis patient during the simulated dialysis treatment, wherein the second user input is associated with a second patient parameter, of the plurality of patient parameters, for the dialysis patient, wherein the second patient parameter is different from the patient parameter; and update a second set of patient parameters of the plurality of patient parameters for the simulated dialysis patient based on the second user input, wherein the second set of patient parameters comprises the second patient parameter associated with the second user input, the blood pressure parameter, and a third patient parameter that is associated with the second patient parameter.

In some examples, initializing the simulated dialysis treatment comprises determining a plurality of dialysis event variables associated with a plurality of dialysis events, and wherein the one or more processors are further configured to: execute one or more dialysis events of the plurality of dialysis events based on comparing a result from a random number generator with one or more dialysis event variables of the plurality of dialysis event variables, and wherein updating the set of patient parameters is further based on executing the one or more dialysis events.

In yet another exemplary embodiment, the present disclosure provides a method, comprising: initializing, by a device and based on a first user input, a simulated dialysis treatment for one or more dialysis patients; receiving, by the device, a second user input for treating a dialysis patient, of the one or more dialysis patients, during the simulated dialysis treatment, wherein the second user input is associated with a patient parameter, of a plurality of patient parameters, for the dialysis patient; updating, by the device, a set of patient parameters of the plurality of patient parameters for the dialysis patient based on the second user input, wherein the set of patient parameters comprises the patient parameter associated with the second user input and one or more additional patient parameters that are associated with the patient parameter, wherein the one or more additional patient parameters comprises a blood pressure parameter indicating a blood pressure of the dialysis patient; causing, by the device, display of an indicia associated with a health of the dialysis patient based on updating the set of patient parameters; and subsequent to completing the simulated dialysis treatment, causing, by the device, display of a prompt indicating a result of the simulated dialysis treatment based on the health of the dialysis patient.

In some instances, the method further comprises: receiving, by the device, a third user input for treating the dialysis patient during the simulated dialysis treatment, wherein the third user input is associated with a second patient parameter, of the plurality of patient parameters, for the dialysis patient, wherein the second patient parameter is different from the patient parameter; and updating, by the device, a second set of patient parameters of the plurality of patient parameters for the dialysis patient based on the third user input, wherein the second set of patient parameters comprises the second patient parameter associated with the third user input, the blood pressure parameter, and a third patient parameter that is associated with the second patient parameter.

In some examples, the one or more additional patient parameters further comprises one or more second patient parameters, wherein the patient parameter and the blood pressure parameter have a relationship with at least one of the one or more second patient parameters.

In some variations, the relationship between the patient parameter and the at least one of the one or more second patient parameters is a direct relationship.

In some instances, the relationship between the patient parameter and the at least one of the one or more second patient parameters is an indirect relationship.

In some examples, the method further comprises during the simulated dialysis treatment, causing, by the device, display of a graphical user interface comprising a plurality of indicia, wherein the plurality of indicia comprises the indicia associated with the health of the dialysis patient and a user-selectable indicia that adjusts the patient parameter, wherein receiving the second user input is based on a user selecting the user-selectable indicia.

In some variations, the patient parameter and the user-selectable indicia are associated with an ultrafiltration rate for the dialysis patient or a heparin amount provided to the dialysis patient.

In some instances, the patient parameter and the user-selectable indicia are associated with adjusting a position of the dialysis patient or an amount of oxygen given to the dialysis patient.

In some examples, initializing the simulated dialysis treatment comprises determining a plurality of dialysis event variables associated with a plurality of dialysis events, and wherein the method further comprises: executing one or more dialysis events of the plurality of dialysis events based on comparing a result from a random number generator with one or more dialysis event variables of the plurality of dialysis event variables, and wherein updating the set of patient parameters is further based on executing the one or more dialysis events.

In some variations, the one or more dialysis events comprises a clotting event indicating the dialysis patient has a clot.

In some instances, the first user input further indicates a level associated with the simulated dialysis treatment, wherein determining the plurality of dialysis event variables is based on the level.

In some examples, the method further comprises: updating one or more of the plurality of dialysis event variables based on executing the one or more dialysis events.

In some variations, the plurality of patient parameters comprises a level of consciousness parameter of the dialysis patient, wherein the method further comprises: determining the health of the dialysis patient based on the blood pressure parameter and the level of consciousness parameter.

In some instances, determining the health of dialysis patient comprises determining whether the level of consciousness parameter indicates the dialysis patient is conscious and the blood pressure parameter being within a blood pressure threshold.

Further features and aspects are described in additional detail below with reference to the figures.

DETAILED DESCRIPTION

Exemplary embodiments of the present application provide a safe and reliable way to improve training for performing dialysis treatments on dialysis machines based on simulation of dialysis treatments using a technological platform implemented through a computer network.

The expertise required to operate dialysis machines and perform dialysis treatment for patients is high, and failures can be catastrophic. Yet, there is currently a shortage of nurses and nephrologists, and the shortage is expected to grow in the future. Therefore, training becomes important for any new nurses, nephrologists, and/or other medical professionals, but with the lack of staff, it is difficult to properly train these new employees. Additionally, technology has improved to permit dialysis treatments to be performed in a patient's home. As such, the patient or another family member may perform the dialysis treatments. But, again, there needs to be certain training to operate these dialysis machines as well as how to prevent to prevent failures during the dialysis treatment.

Currently, there is corporate training for performing dialysis treatments, but these are typically fairly static with always a "correct answer" (e.g., a multiple choice question with a correct answer). But, during actual dialysis treatments, events may occur and complications may happen, which may require fast thinking to avoid failure and possibly discomfort or even death for a patient. For instance, patients may unexpectedly be rendered unconscious by the dialysis treatment due to low blood pressure and a user may need to figure out the reason behind why the patient was rendered unconscious as well as next steps to ensure the patient's safety. As such, the present disclosure provides a system and method for operators (e.g., users), including new nurses or nephrologists as well as patients or their family members, to learn the intricacies of dialysis (e.g., hemodialysis) treatment through a simulation. The simulation may afford them the ability to fail catastrophically, see the consequences, learn and internalize complex algorithms, and develop the ability to think in a time pressured situation.

In some instances, the present disclosure may provide a simulation that is in a mobile application form factor to encourage more ubiquitous use on personal devices, which may provide ease of access for the dialysis training. In some examples, the present disclosure may include a time-based simulated scenarios that increase in difficulty and complexity between levels. In some variations, the present disclosure may provide a safe learning environment for experiencing decisions and consequences of these decisions when performing dialysis treatment.

Figure 1:
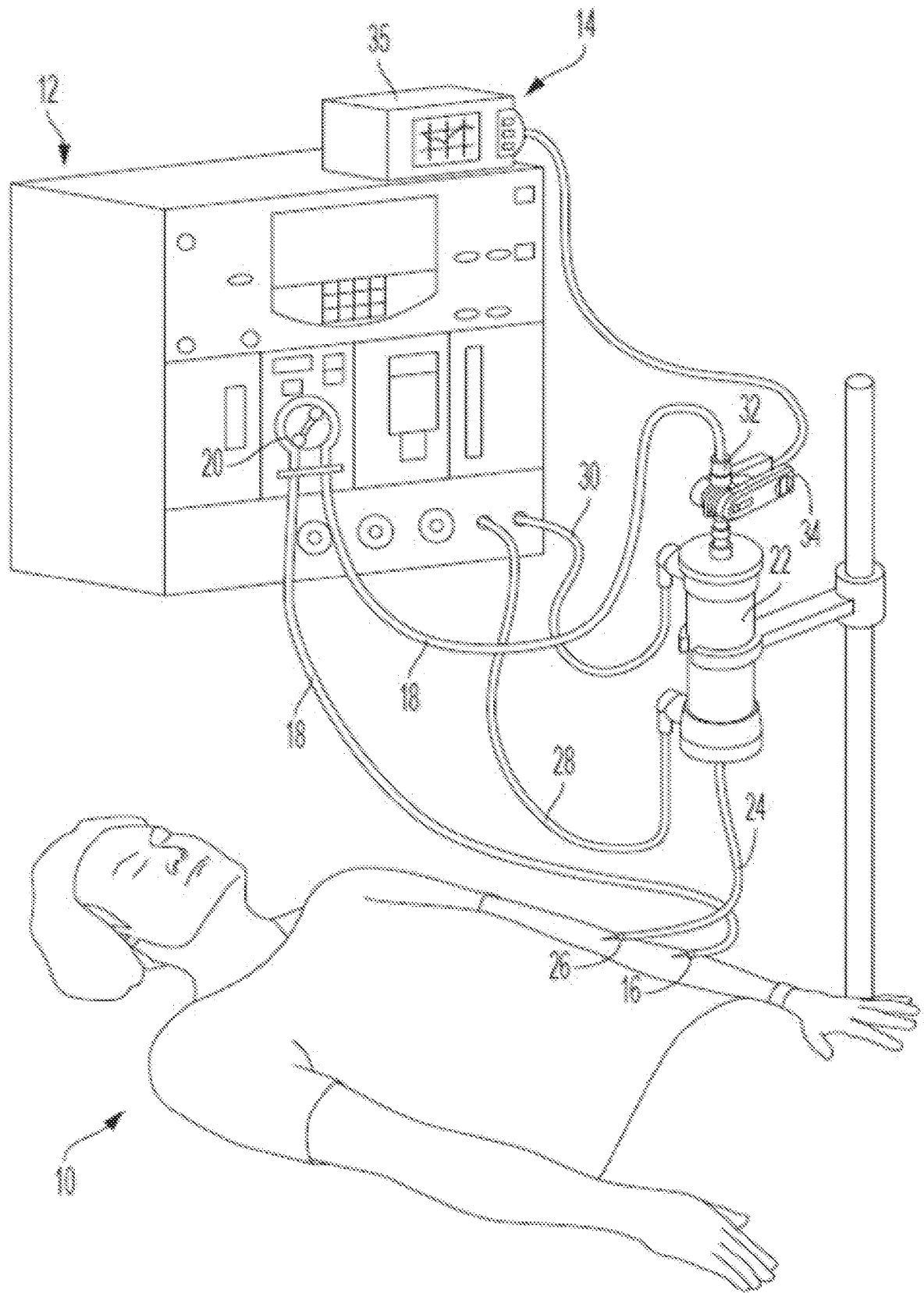
FIG. 1 is a schematic diagram of an exemplary medical treatment system according to one or more examples of the present application.

FIG. 1 is a schematic diagram of an exemplary medical system (e.g., a dialysis system) according to one or more examples of the present application. By way of example, the medical system shown in FIG. 1 is a hemodialysis system; however, other medical systems are contemplated. The hemodialysis system may be used to measure/determine hematocrit (HCT), hemoglobin (HGB), and/or absolute blood volumes (ABV) of a patient 10. For example, FIG. 1 depicts a patient 10 undergoing hemodialysis treatment using a hemodialysis machine 12. The hemodialysis system further includes an optical blood monitoring system 14.

An inlet needle or catheter 16 is inserted into an access site of the patient 10, such as in the arm, and is connected to extracorporeal tubing 18 that leads to a peristaltic pump 20 and to a dialyzer 22 (or blood filter). The dialyzer 22 removes toxins and excess fluid from the patient's blood. The dialyzed blood is returned from the dialyzer 22 through extracorporeal tubing 24 and return needle or catheter 26. In some parts of the world, the extracorporeal blood flow may additionally receive a heparin drip to prevent clotting. The excess fluids and toxins are removed by clean dialysate liquid which is supplied to the dialyzer 22 via tube 28, and waste liquid is removed for disposal via tube 30. A typical hemodialysis treatment session takes about 3 to 5 hours in the United States.

The optical blood monitoring system 14 includes a display device 35 and a sensor device 34. The sensor device 34 may, for example, be a sensor clip assembly that is clipped to a blood chamber 32, wherein the blood chamber 32 is disposed in the extracorporeal blood circuit. A controller (e.g., processor) of the optical blood monitoring system 14 may be implemented in the display device 35 or in the sensor clip assembly 34, or both the display device 35 and the sensor clip assembly 34 may include a respective controller for carrying out respective operations associated with the medical system.

The hemodialysis machine 12 may also include or be connected to a display, a user input interface, and one or more processors for carrying out dialysis treatments and/or for simulating dialysis treatments. The user input interface may be used, for example, to control components of the hemodialysis machine 12 and/or to control aspects of a dialysis treatment being performed using the machine and/or to control aspects of a simulated dialysis treatment. The one or more processors may, for example, execute treatment routines or simulations thereof. The user input interface may include, for example, physical buttons and/or a touch-sensitive portion of a touchscreen display. The display may be configured, for example, to display information relating to components of the machine, an ongoing dialysis treatment, or a simulated dialysis machine.

The blood chamber 32 may be disposed in line with the extracorporeal tubing 18 upstream of the dialyzer 22. Blood from the peristaltic pump 20 flows through the tubing 18 into the blood chamber 32. The sensor device 34 includes emitters that emit light at certain wavelengths and detectors for receiving the emitted light after it has passed through the blood chamber 32. For example, the emitters may include LED emitters that emit light at approximately 810 nm, which is isobestic for red blood cells, at approximately 1300 nm, which is isobestic for water, and at approximately 660 nm, which is sensitive for oxygenated hemoglobin, and the detectors may include a silicon photodetector for detecting light at the approximately 660 and 810 nm wavelengths, and an indium gallium arsenide photodetector for detecting light at the approximately 1300 nm wavelength. The blood chamber 32 includes lenses or viewing windows that allows the light to pass through the blood chamber 32 and the blood flowing therein.

An example of an optical blood monitoring system having a sensor clip assembly configured to measure hematocrit and oxygen saturation of extracorporeal blood flowing through a blood chamber is described in U.S. Pat. No. 9,801,993, titled "SENSOR CLIP ASSEMBLY FOR AN OPTICAL MONITORING SYSTEM," which is incorporated by reference in its entirety herein.

A controller of the optical blood monitoring system 14 uses the light intensities measured by the detectors to determine HCT values for blood flowing through the blood chamber 32. The controller calculates HCT, HGB, oxygen saturation, and change in blood volume (e.g., ABV) associated with blood passing through the blood chamber 32 to which the sensor device 34 is attached using a ratiometric model. The intensity of the received light at each of the various wavelengths is reduced by attenuation and scattering from the fixed intensity of the visible and infrared light emitted from each of the LED emitters. Beer's Law, for each wavelength of light, describes attenuation and scattering as follows:

$$i_n = I_{0-n} * e^{-\epsilon_p X_p d_{pt}} * e^{-\epsilon_b X_b d_b} * e^{-\epsilon_p X_p d_{pr}} \qquad \text{Eq.(1)}$$

where $i_n$=received light intensity at wavelength n after attenuation and scattering; $I_{0-n}$=transmitted light intensity at wavelength n incident to the measured medium; e=the natural exponential term; ε=the extinction coefficient for the measured medium (p—blood chamber polycarbonate, b—blood); X=the molar concentration of the measured medium (p—blood chamber polycarbonate, b—blood); and d=the distance through the measured medium (pt—transmitting blood chamber polycarbonate, b—blood, pr—receiving blood chamber polycarbonate).

Since the properties of the polycarbonate blood chamber do not change, the first and third exponential terms in the above Eq. (1) are constants for each wavelength. Mathematically, these constant terms are multiplicative with the initial constant term $I_{0-n}$ which represents the fixed intensity of the radiation transmitted from a respective LED emitter. For simplification purposes, Eq. (1) can be rewritten in the following form using bulk extinction coefficients and a modified initial constant $I'_{0-n}$ as follows:

$$i_n = I'_{0-n} * e^{-\alpha_b d_b} \qquad \text{Eq. (2)}$$

where $i_n$=received light intensity at wavelength "n" after attenuation and scattering as though the detector were at the receive blood boundary; $\alpha$=the bulk extinction coefficient ($\alpha_b = \varepsilon_b X_b$) and $I'_{0-n}$=the equivalent transmitted light intensity at wavelength n as if applied to the transmit blood boundary accounting for losses through the blood chamber. Note that the term $I'_{0-n}$ is the light intensity incident on the blood with the blood chamber losses included.

Using the approach defined in Eq. (2) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values $\alpha$ for the red blood cells and the water constituents in the blood chamber, respectively. A mathematical function then defines the measured HCT value:

$$HCT = f\left[\frac{\ln\left(\frac{i_{810}}{I_{0\text{-}810}}\right)}{\ln\left(\frac{i_{1300}}{I_{0\text{-}1300}}\right)}\right] \qquad \text{Eq. (3)}$$

where $i_{810}$ is the light intensity of the photo receiver at 810 nm, $i_{1300}$ is the infrared intensity of the photodetector at 1300 nm and $I_{0\text{-}810}$ and $I_{0\text{-}1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = f\left[\frac{\ln\left(\frac{i_{810}}{I_{0\text{-}810}}\right)}{\ln\left(\frac{i_{1300}}{I_{0\text{-}1300}}\right)}\right] = A\left[\frac{\ln\left(\frac{i_{810}}{I_{0\text{-}810}}\right)}{\ln\left(\frac{i_{1300}}{I_{0\text{-}1300}}\right)}\right]^2 + B\left[\frac{\ln\left(\frac{i_{810}}{I_{0\text{-}810}}\right)}{\ln\left(\frac{i_{1300}}{I_{0\text{-}1300}}\right)}\right] + C. \qquad \text{Eq. (4)}$$

A second order polynomial is normally adequate as long as the infrared radiation incident at the first and second wavelengths is substantially isobestic.

After the HCT value has been determined by a controller at the sensor device 34 or at the display device 35, the display device may be used to output the determined HCT value. Further, the controller may further determine an HGB concentration value based on the determined HCT value, with the HGB concentration value also being output on the display device 35.

For instance, the HGB for a blood sample corresponds to the mass of protein (e.g., in grams) for the blood sample, and an HGB concentration value corresponds to a protein mass per unit of blood sample volume. The HGB concentration value may be determined based on multiplying an HCT value and a mean corpuscular hemoglobin concentration (MCHC) value. It will be appreciated that the HCT value corresponds to the volume of red blood cells (RBCs) in a blood sample divided by the total volume of the blood sample, and that the MCHC value corresponds to an average mass of HGB per RBC divided by an average volume per RBC. It will further be appreciated that the MCHC value corresponds to mean corpuscular hemoglobin (MCH) divided by mean corpuscular volume (MCV), wherein MCH corresponds to an average mass of HGB per RBC of a patient (e.g., in picograms), and wherein MCV corresponds to an average volume per RBC of a patient (e.g., in femtoliters). Thus, when the HCT value is multiplied by the MCHC value, the HGB concentration value that is determined corresponds to a protein mass per unit of blood sample volume.

The medical system (e.g., hemodialysis system) depicted in FIG. 1 may be one of a plurality of medical systems in a dialysis clinic and/or in ICUs. Patients may come into the dialysis clinic for treatments at regular intervals, for example, on a Monday-Wednesday-Friday schedule or a Tuesday-Thursday-Saturday schedule. In some instances, the medical system depicted in FIG. 1 may be within a patient's home.

It will be appreciated that the medical system depicted in FIG. 1 is merely exemplary. The principles discussed herein may be applicable to other medical systems in which treatment operations are performed through a user interface.

Figure 2:
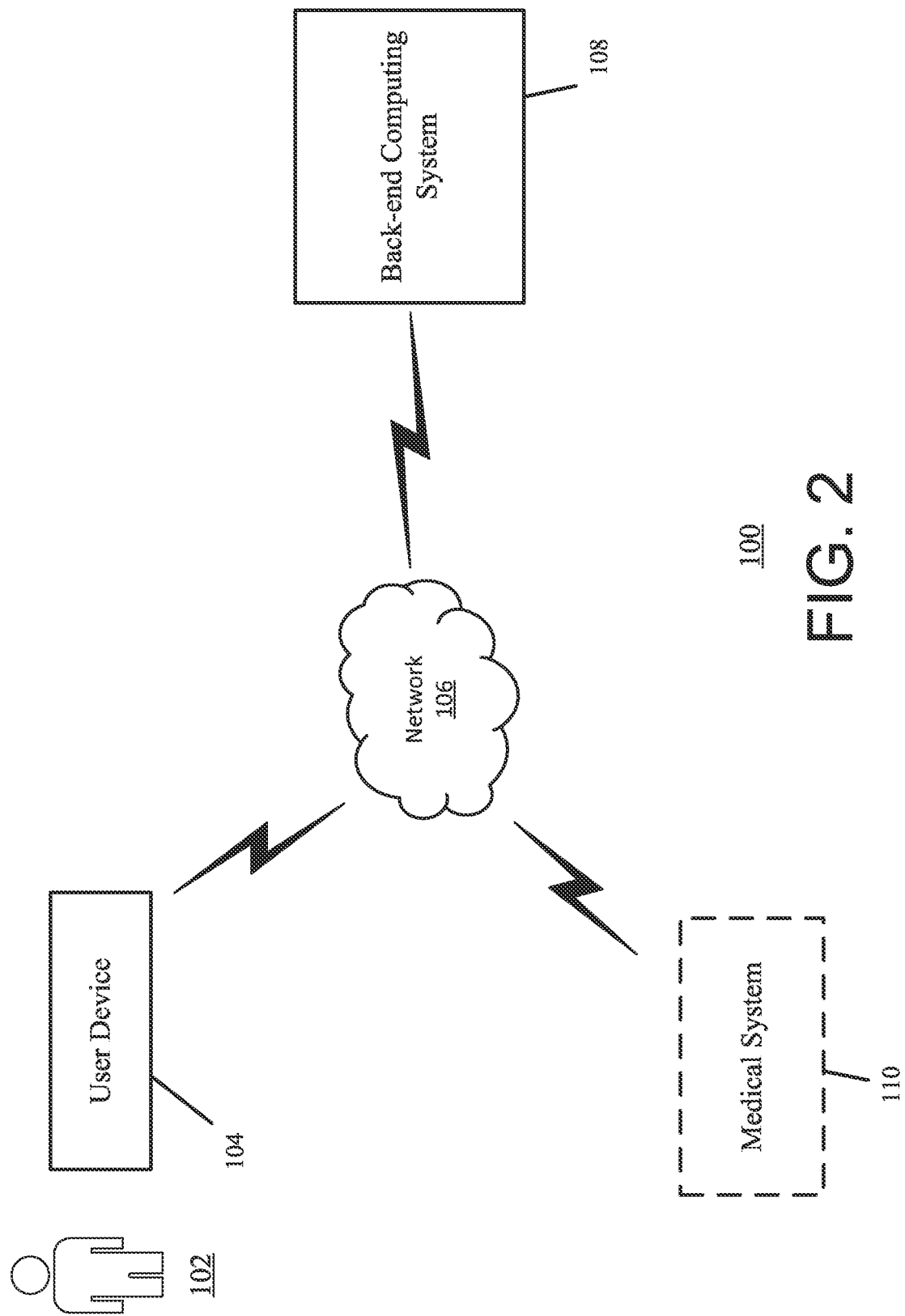
FIG. 2 is a block diagram depicting an exemplary computing environment in accordance with one or more examples of the present application according to one or more examples of the present application.

FIG. 2 is a block diagram depicting an exemplary computing environment in accordance with one or more examples of the present application. The environment 100 includes a user (e.g., a nurse, doctor, medical professional, patient, family member of the patient, and/or other users) 102, a user device (e.g., mobile device) 104 associated with the user 102, a back-end computing system 108, and a medical system 110. Although the entities within environment 100 may be described below and/or depicted in the figures as being singular entities, it will be appreciated that the entities and functionalities discussed herein may be implemented by and/or include one or more entities.

The entities within the environment 100 such as the user device 104, the back-end computing system 108, and the medical system 110 may be in communication with other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100.

The medical system 110 is denoted in a dashed box to indicate that the medical system 110 is optional within the environment 100. When present, the medical system 110 may be the medical system depicted in FIG. 1 (e.g., the medical system 110 may be or include a dialysis/hemodialysis machine that performs dialysis treatment). The medical system 110 may provide and/or receive information from other entities within the environment 100 (e.g., the back-end computing system 108 and the user device 104).

The back-end computing system 108 is a computing system that is associated with an enterprise organization. The enterprise organization may be any type of corporation, company, organization, and/or other institution. The back-end computing system 108 includes one or more computing devices, computing platforms, systems, servers, and/or other apparatuses capable of performing tasks, functions, and/or other actions for the enterprise organization. In some instances, the back-end computing system 108 may, for example, communicate with the user device 104. For instance, the back-end computing system 108 may store a software application and provide the software application to the user device 104. When executed, the software application may simulate dialysis treatment for one or more patients. For example, the back-end computing system 108 may be associated with and/or operate an application database, and the user device 104 may download the dialysis simulation software application from the back-end computing system 108. Additionally, and/or alternatively, the back-end computing system 108 may be operated by an enterprise organization that is associated with the medical system 110 and provides training for the medical system 110 such as provide training for dialysis treatments. The back-end computing system 108 may provide the dialysis simulation software application to the user device 104 to provide dialysis training to the user 102.

The back-end computing system 108 may be implemented using one or more computing platforms, devices, servers, and/or apparatuses. In some variations, the back-end computing system 108 may be implemented as engines, software functions, and/or applications. In other words, the functionalities of the back-end computing system 108 may be implemented as software instructions stored in storage (e.g., memory) and executed by one or more processors.

The user 102 may operate, own, and/or otherwise be associated with a user device 104. For instance, the user device 104 may be a mobile phone such as a smartphone that is owned and/or operated by the user 102. The user 102 may provide information to the other entities of environment 100 such as the back-end computing system 108 using the user device 104. For example, the user device 104 may receive user input from the individual 102 such as indications to download, operate, and/or manage a software application associated with the enterprise organization. The software application may be an application that simulates dialysis treatment for one or more patients. This will be described in further detail below.

The user device 104 may be and/or include, but is not limited to, a desktop, laptop, tablet, mobile device (e.g., smartphone device, or other mobile device), smart watch, an internet of things (JOT) device, or any other type of computing device that generally comprises one or more communication components, one or more processing components, and one or more memory components. The user device 104 may be able to execute software applications managed by, in communication with, and/or otherwise associated with the enterprise organization. In some instances, the user device 104 may be a computing device that includes a user input interface (e.g., a mouse, keyboard, graphical user interface, and/or other types of devices or components that are capable of detecting user input and providing the user input to a processor), a display for displaying information, one or more processors, and/or memory.

In some instances, the user device 104 may provide display screens (e.g., the display screens shown on FIGS. 5A and 5B) with regions (e.g., buttons) for the user to provide input. For instance, the user device 104 may provide a graphical user interface that allows the user to input feedback to adjust certain conditions during dialysis treatment such as giving the patient saline or adjusting the arterial and/or venous pressure of a patient. Based on the user feedback, the user device 104 may simulate the dialysis treatment for the patient, which will be explained in further detail below.

In some examples, the user device 104 (e.g., a desktop or laptop) may provide a simulated environment that includes a dialysis machine such as the dialysis machine described in FIG. 1. The simulated dialysis machine may include buttons that when pressed, update the patient's conditions. For instance, in the simulated environment, the user 102 may move around the simulated dialysis machine to perform the dialysis treatment. In other words, instead of having a graphical user interface with buttons, the user device 104 may provide a simulated environment with a dialysis machine and a patient such that the user 102 is able to perform dialysis treatment on the patient using the simulated dialysis machine. In some instances, the user device 104 may further provide an option for the user 102 to select the specific model of the dialysis machine that is included within the simulated environment. As such, the user device 104 may display an actual dialysis machine that is used to train the user 102.

In some variations, the user device 104 may use a virtual reality (VR) or an augmented reality (AR) to train the user 102 in performing dialysis treatment. For instance, the user device 104 may display an AR or VR environment that includes a dialysis machine, and may train the user 102 using the AR/VR environment. For example, the user 102 may move around the AR/VR environment and provide user feedback (e.g., via an AR or VR device such as a VR glove) such as mimicking the actions to insert or re-insert a needle into the patient's arm to begin dialysis treatment. Furthermore, the user 102 may provide user feedback such as mimicking providing saline or oxygen to the patient and/or perform functionalities on the dialysis machine within the AR/VR environment such as mimicking providing heparin to the patient. In other words, the user device 104 may provide an AR/VR environment for training the user 102 to perform dialysis treatments on a simulated dialysis machine.

It will be appreciated that the exemplary environment depicted in FIG. 2 is merely an example, and that the principles discussed herein may also be applicable to other situations—for example, including other types of institutions, organizations, devices, systems, and network configurations.

Figure 3:
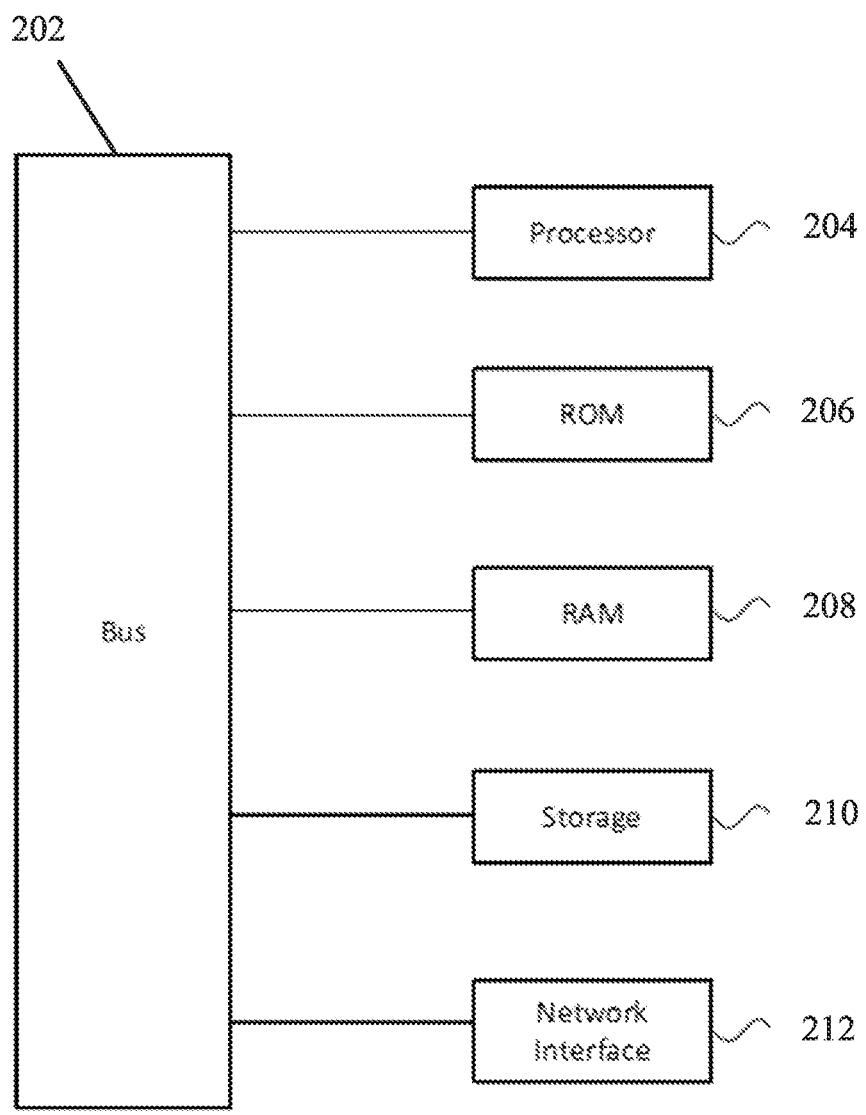
FIG. 3 is a block diagram of one or more devices or systems within the exemplary environment of FIG. 2 according to one or more examples of the present application.

FIG. 3 is a block diagram of one or more devices or systems within the exemplary environment of FIG. 2 according to one or more examples of the present application. For instance, the device/system 200 may be the user device 104 of FIG. 2. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component, server, device, computing platform, and/or computing apparatus within the device/system 200. Additionally, and/or alternatively, the device/system 200 may further include components that might not be included within every entity of environment 100.

Figure 4:
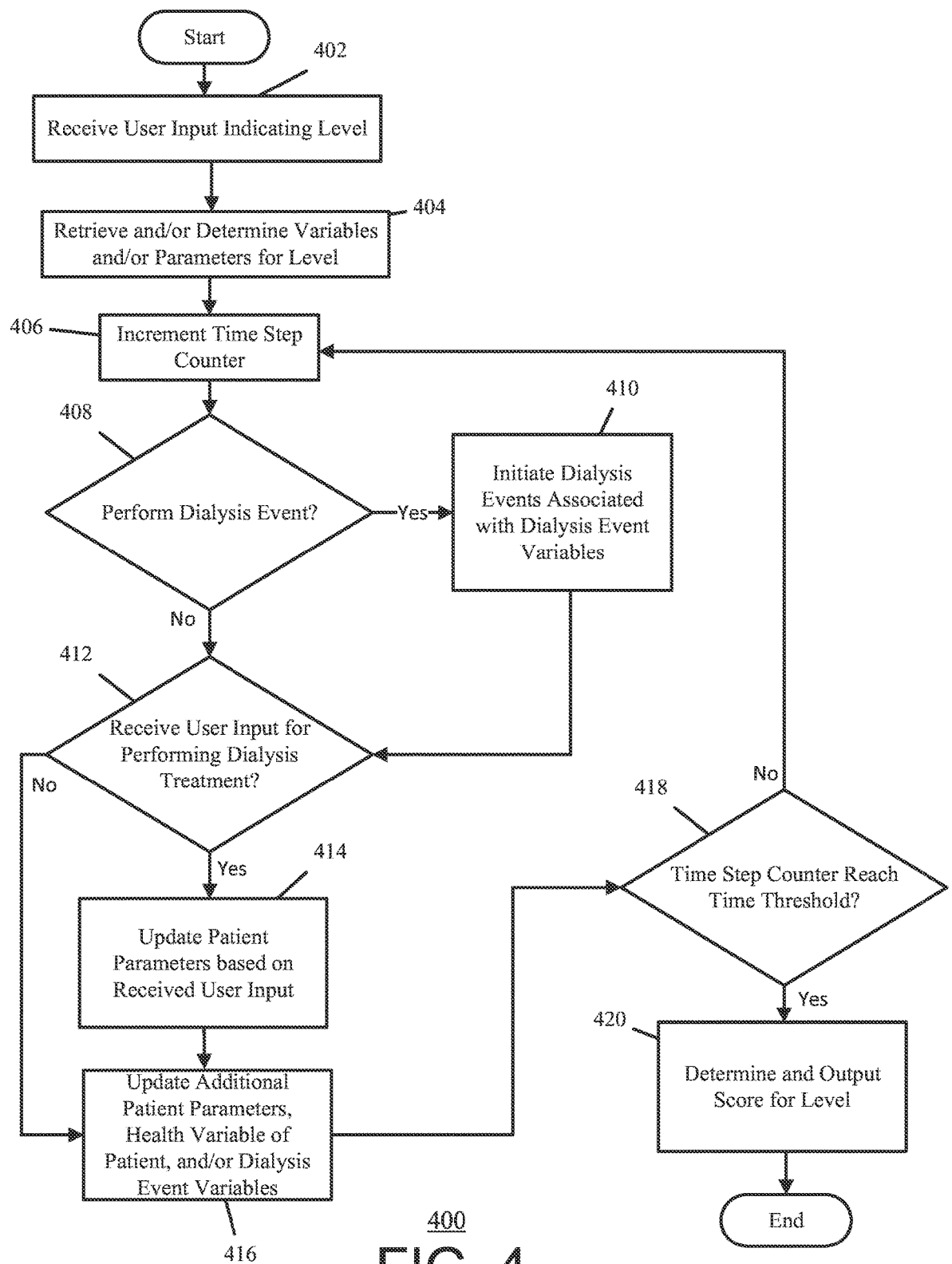
FIG. 4 is a flowchart of an exemplary process for training a user by simulating dialysis treatments according to one or more examples of the present application.

FIG. 4 is a flowchart of an exemplary process for training a user by simulating dialysis treatments according to one or more examples of the present application. The process may be performed by a user device such as the user device 104 depicted in FIG. 2. However, it will be recognized that any of the following blocks may be performed in any suitable order, and that the process 400 may be performed in any suitable environment. The descriptions, illustrations, and processes of FIG. 4 are merely exemplary and the process 400 may use other descriptions, illustrations, and processes for providing dialysis treatment training.

Prior to starting process 400, the user device 104 may obtain the software application from the back-end computing system 108. After obtaining the software application and to begin process 400, the user device 104 may begin executing the instructions of the software application. The software application is a dialysis treatment simulation application and configured to provide training for the user 102. For example, the dialysis treatment simulation application (application) may include a plurality of levels that are time sensitive (e.g., each level may be a certain length of time such as four minutes). The goal of the application may include keeping the patients under the user's 102 care conscious, remove enough fluid within the patient to get the patient to their estimated dry weight (EDW), keep the patient on the dialysis treatment for the duration of the prescribed treatment length, get the patients on/off their dialysis treatments on time, and/or additional or alternative goals. After completing each level, the user device 104 may output a prompt indicating a score for the user 102. The score may be based on one or more factors such as, but not limited to, percentage of time on actual treatment (tx)/ prescribed treatment (rx) (e.g., the percentage of the prescribed treatment time completed), volume removed (%), conscious amount/time (%), success of on/off times (%). For instance, the user device 104 may calculate a score based on the one or more factors and provide a numerical output (e.g., a number of points out of 100) for the score and/or a star rating (e.g., a rating out of five stars).

At block 402, the user device 104 receives user input indicating a level for the simulated dialysis treatment. For instance, the dialysis treatment simulation application may include a plurality of levels that gradually increases in difficulty for the user 102 as the user 102 progresses through their training. For example, the levels may indicate a number of dialysis patients for the user 102 to take care of, a difficulty associated with each of the patients, a plurality of patient parameters for the patients, dialysis event variables associated with dialysis events for the patients, and/or additional information.

In some variations, the difficulty of the patient may indicate a number of complications for the patient. For instance, for a patient with an easy difficulty, the patient may have zero complications. For a medium difficulty, the patient may have one complication. For a hard difficulty, the patient may have two complications, and so on. The complications for the patient may include, but are not limited to, a high fluid goal, clotting issues, behavioral issues, variable refill, blood pressure sensitive, educational needs, difficulty with access (e.g., the patient's skin may be difficult to penetrate with a needle or to find an insertion point for the needle), and so on. For instance, a patient with behavior issues may be more argumentative. A patient with a blood pressure sensitivity complication may be more sensitive to having fluid removed during the dialysis treatment (e.g., user inputs may more severely influence the blood pressure of the patient).

Further, each of the complications (e.g., comorbidities and/or psychological factors) may be associated with a plurality of dialysis events. For example, a patient with a behavioral issue complication may have an associated dialysis event indicating that the patient wants off of the dialysis treatment. If left untreated (e.g., without adequate user feedback), the patient may have additional dialysis events such as disconnecting themselves from the dialysis machine. Additionally, and/or alternatively, a patient with clotting issues may have an associated dialysis event such as clotting during the dialysis treatment. The user 102 may adjust the heparin for the patient and/or give the patient saline to alleviate the clotting event.

In some instances, one or more dialysis events might not be associated with a complication. For instance, a dialysis event may include a needle becoming disconnected from the patient. In other words, there may be dialysis events for a patient regardless of the complications for the patient.

The plurality of dialysis events may include, but are not limited to, a sudden low blood pressure event (e.g., due to the blood pressure sensitivity complication, the patient may have a hard time keeping up with fluid removal and their blood pressure may drop easily), a clotting event (e.g., due to the clotting complication, the patient may have clotting events that interfere with the dialysis treatment), a behavioral event (e.g., the patient may get impatient with the treatment length or are otherwise easily frustrated), a complex access event (e.g., the access of a patient may have turns and/or other structural issues that interfere with needle placement and access flow), needle displacement event (e.g., the needle bevel may get lodged against the side of the access or the needle may come out altogether), a cardiac event (e.g., the patient may suffer a heart attack or stroke), a lifestyle compliance variation event (e.g., the patient may take in excess fluid between treatments and/or miss treatments), a high ultrafiltration rate (UFR) event (e.g., the UFR of the patient is too high and the patient cannot keep up), and/or equipment/water events (e.g., regardless of the patient, there may be equipment or water issues that occur during the dialysis treatment).

Figure 6:
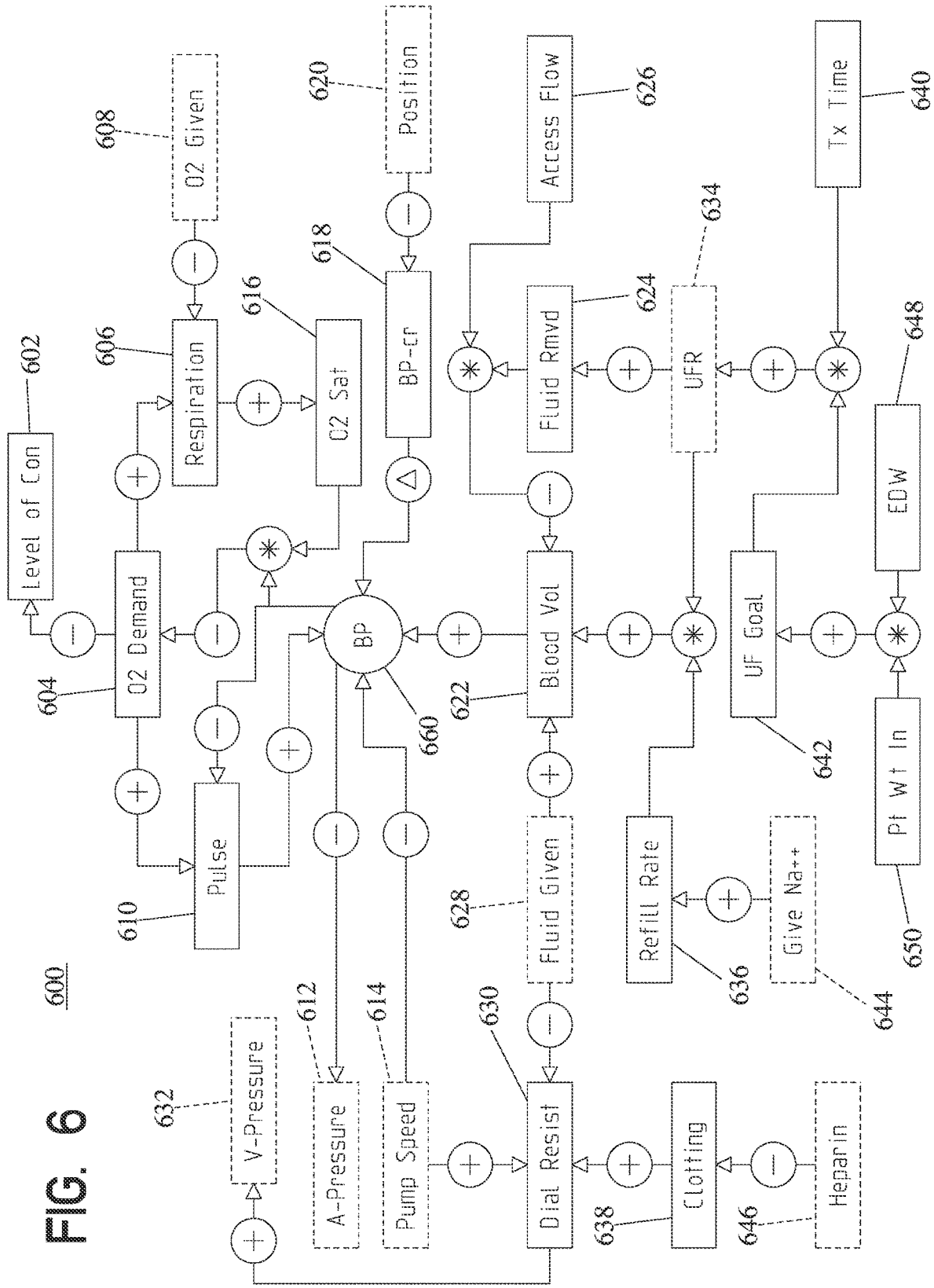
FIG. 6 is a graphical representation of exemplary interconnectivity and relationships between the patient parameters according to one or more examples of the present application.

The plurality of patient parameters are parameters or measurements associated with a particular patient. For instance, the patient parameters may include, but are not limited to, oxygen levels of the patient, the pump speed, the arterial pressure, the venous pressure, the EDW, and/or additional patient parameters that are shown in FIG. 6 and described below. Each of the patient parameters may have one or more relationships with one or more other patient parameters. For instance, the pump speed for the dialysis machine may relate to the blood pressure of the patient. In other words, if the user 102 provides user input to adjust the pump speed, the blood pressure may be adjusted/updated as well. The patient parameters and their relationships will be described in FIG. 6 below.

To put it another way, in some instances, the application includes a plurality of levels. For instance, the first level (e.g., the easiest level that the user 102 initially starts on and/or a tutorial level) may include only one patient that has a patient difficulty of easy. The patient difficulty of easy may indicate that they have no complications (e.g., zero or very few dialysis events). The second level may also include one patient, but the patient may have a patient difficulty of medium. The patient difficulty of medium may indicate one complication (e.g., one or more dialysis events associated with the one complication). The third level may have one patient with a patient difficulty of hard, which is associated with two complications (e.g., one or more dialysis events associated with each of the two complications). The fourth level may include two patients with one patient having an easy difficulty and another patient having a medium difficulty. The application may include a plurality of levels and as the user 102 completes each level (e.g., having a calculated score above a score threshold), a new level may be unlocked for the user 102.

In some variations, the application may include a total of 18 levels. The 18 levels may be broken up as follows: 1) one patient (easy (e)); 2) one patient (medium (m)); 3) one patient (hard (h)); 4) two patients (e, m); 5) two patients (m, h); 6) three patients (e, e, m); 7) three patients (e, m, h); 8) three patients (m, h, h); 9) four patients (e, m, m, h); 10) four patients (m, m, h, h); 11) five patients (e, m, m, h, h); 12) five patients (m, m, m, h, h); 13) five patients (m, m, h, h, h); 14) six patients (e, m, m, h, h, h); 15) six patients (m, m, m, h, h, h); 16) six patients (m, m, h, h, h, h); 17) six patients (m, h, h, h, h, h); 18) six patients (h, h, h, h, h, h). In other words, each of the levels indicates a number of patients and a difficulty associated with each patient (e.g., for level 9, there are four patients—one easy, two medium, and one hard).

The levels, patient difficulties, number of patients, patient parameters, and dialysis events described above are merely exemplary, and the application include any number or type of levels, patient difficulties, number of patients, patient parameters, and dialysis events. For instance, each of the patients may include one or more of the same dialysis events, including all of the same dialysis events. However, the likelihood of initiating the events (e.g., the dialysis event variables described below) may differ based on the difficulty level and/or the complications. For example, based on the complication indicating clotting issue, the clotting event may increase in likelihood (e.g., the dialysis event variable may be increased). Additionally, and/or alternatively, the clotting event may increase in likelihood based on the difficulty (e.g., easy difficulty may have a lower probability when compared to medium difficulty and high difficulty). Additionally, and/or alternatively, the clotting event may be more severe based on the difficulty level. For instance, for easy difficulty, the clotting event may be less severe such that the user 102 may only need to adjust the heparin to resolve the event. For high difficulty, the user 102 may need to adjust the saline and/or other parameters for the patient in order to resolve the event.

At block 404, the user device 104 retrieves and/or determines variables (e.g., dialysis event variables) and/or parameters (e.g., patient parameters) for the selected level. For instance, based on the level indication (e.g., level 5), the user device 104 may determine the dialysis event variables associated with the dialysis events (e.g., the variables associated with the dialysis events for both the medium patient, which has one complications, and for the hard patient, which has two complications) and the patient parameters for the one or more patients (e.g., the patient parameters for the medium patient and the hard patient).

The retrieved dialysis event variables may indicate a likelihood for a dialysis event to occur. For instance, the dialysis event variable may be a numerical value between 0-100. Based on comparing the dialysis event variable with a value from a random number generator, the user device 104 may determine whether to execute or initiate the dialysis event (e.g., patient complaining to be taken off of the dialysis treatment or patient being rendered unconscious). In some instances, different complications (e.g., comorbidities or psychological factors) may have the same dialysis event, but with different assigned dialysis event variables. For instance, if the patient has a clotting issue complication, the dialysis event variable for the dialysis event of patient complaining to be taken off of dialysis treatment may be low (e.g., a value of 10) or there may be no dialysis event for such a complication. But, the dialysis event variable for the patient having a clot may be high (e.g., a value of 70). If the patient has a behavioral issue complication, the dialysis event variable for the dialysis event of patient of patient complaining to be taken off of dialysis treatment may be high (e.g., a value of 80) whereas the dialysis event variable for the patient having a clot may be low (e.g., value of 20).

Additionally, and/or alternatively, the difficulties associated with the patients may impact the dialysis event variables. For instance, an easy difficulty patient may have a low dialysis event variable (e.g., value of 10) for a needle becoming disconnected from the patient during the dialysis treatment whereas a hard difficulty patient may have a high dialysis event variable (e.g., value of 60) for the same dialysis event.

In some variations, the dialysis event variables for a patient may be in a matrix data format such as a 3×3 matrix indicating the three difficulties (e.g., easy, medium, and hard) and three problem areas (e.g., three complications such as clotting issues, blood pressure sensitivity, and behavioral issues). The dialysis event variables for the events may be included within the data matrix. For instance, each entry for the matrix may indicate one or more dialysis event variables associated with a particular difficulty and a particular problem area. The user device 104 may retrieve the matrix at block 404.

The user device 104 further retrieves an initial set of patient parameters. The patient parameters may indicate an EDW for the patients (e.g., a first EDW for the medium patient and a second EDW for the hard patient), a predefined value or starting range for the patient parameters, a prescription for a duration of the dialysis treatment and an ultrafiltration (UF) profile (e.g., a UF rate for the patient), and a history note. The history note may include a simplified write-up of the patient indicating one or more complications for the patient (e.g., previous behavioral issues). The user 102 may select the history note and the user device 104 may display information associated with the patient. The user device 104 may store a plurality (e.g., three or four dozen) patient avatars, and each patient avatar may include a history note for the patient as well as other information such as the biometrics of the patient and/or the dialysis event variables.

In some examples, the user device 104 may retrieve a specific value or number for the patient parameters and/or the dialysis event variables. In other examples, the user device 104 may retrieve a range for the patient parameters and/or the dialysis event variables (e.g., between 10-20). The user device 104 may then determine (e.g., randomly assign) a value within the range for the patient (e.g., randomly assign a value of 16 for the patient parameter and/or the dialysis event variable).

In some variations, the user device 104 may store the retrieved patient parameters and/or dialysis event variables in an array. The array may indicate the current values and next values. For instance, initially, the current values may be the retrieved patient parameters and/or dialysis event variables from memory. Then, based on blocks 406-418 described below, the user device 104 may update the patient parameters and/or dialysis event variables and include them in the next values. In the following iteration, the user device 104 may place the next values into the current value slots, and use these next values. The user device 104 may further determine the next values again in a continuous loop.

After retrieving and/or storing the patient parameters and/or the dialysis event variables, the user device 104 may begin the simulated dialysis treatment for the patient. For example, each level may last for a certain amount of time (e.g., four or five minutes) and may be broken into time steps (e.g., five or ten second increments). At each of the time steps, the user device 104 may perform blocks 406 through 418 below. To put it another way, the user device 104 may use a time step counter to determine whether to end a particular level (e.g., move to block 420). Alternatively, if all of the patients have reached their goal (e.g., their EDW), the particular level may also end (e.g., move to block 420).

During block 406-418, the user device 104 may continuously determine whether to initiate dialysis events, update the dialysis event variables and/or patient parameter variables, and output indicia associated with the patient parameter variables. In other words, the user device 104 may simulate dialysis treatment for one or more patients by updating the patient parameter variables and outputting indicia associated with the dialysis treatments.

For instance, at block 406, the user device 104 increments a time step counter. In particular, as mentioned above, each level may last a certain amount of time (e.g., four minutes). Each time process 400 reaches block 406, the user device 104 may increase a time step counter by a time step (e.g., five or ten seconds).

At block 408, the user device 104 determines whether to perform one or more dialysis events. For instance, as mentioned previously, each of the dialysis event variables may be associated with a dialysis event such as the patient having a clot, the patient wanting to be taken off dialysis treatment, and/or a needle becoming loose and falling out. The user device 104 may use a random number generator and compare the result(s) from the random number generator with the dialysis event variables to determine whether to initiate one or more dialysis events. For instance, the random number generator may output a number from one to one hundred (e.g., 55). The user device 104 may compare the output from the random number generator with the dialysis event variable (e.g., 60) to determine whether to initiate the dialysis event. For example, based on the output being less than the dialysis event variable, the user device 104 may determine to initiate the event and process 400 moves to block 410. As such, the likelihood of initiating an event may be based on the dialysis event variable. Initiating a dialysis event by using a random number generator is merely exemplary and the user device 104 may use other methods, algorithms, or processes to determine whether to initiate dialysis events.

Based on determining whether to perform the dialysis event, the process 400 moves to either block 410 or 412. For instance, based on determining to perform the dialysis event, process 400 moves to block 410 and the user device 104 initiates one or more dialysis events associated with the dialysis event variable.

At block 410, the user device 104 initiates the dialysis events associated with the dialysis event variables. For example, based on the dialysis event variable indicating a needle coming loose and falling out, the user device 104 provides a prompt to the user 102 indicating the event. The prompt may be displayed on the display of the user device 104 and may indicate the event such as a needle has come loose or the patient has indicated he or she wants to stop the dialysis treatment.

In some instances, the user device 104 may initiate a high UFR event. For instance, the user device 104 may cause a prompt indicating that the patient's UFR is set too high and exceeds the refill rate. Further, based upon initiating the event, the user device 104 may increase the patient's UFR, decrease the blood volume parameter (e.g., the blood volume parameter 622 in FIG. 6), which causes a decrease in the blood pressure (e.g., the blood pressure 660 in FIG. 6) and causes the arterial pressure (e.g., arterial pressure 612 in FIG. 6) on the machine to decrease. Due to this, the patient's body may increase the pulse (e.g., the pulse 610 in FIG. 6) in an attempt to circulate more oxygen, which increases the demand for oxygen (e.g., O2 demand 604 in FIG. 6) and potentially decreases the patient's level of consciousness (e.g., the level of consciousness 602).

In some instances, the user device 104 may initiate a clotting event. For instance, the user device 104 may cause a prompt indicating a clot. Further, based on initiating the event, the user device 104 may increase the dialyzer resistance (e.g., the dialyzer resistance 630 in FIG. 6) due to the reduced throughput caused by the clotting, which may increase the venous pressure (e.g., the venous pressure 632 in FIG. 6) on the machine.

At block 412, the user device 104 determines whether user input has been received for performing the dialysis treatment. For instance, in some instances, based on initiating a clotting event, the user 102 may provide user input to slow the pump (e.g., slow the pump speed 614 in FIG. 6) and return 200 milliliters (mL) of fluid (e.g., the fluid given 628 in FIG. 6) back into the system to flush the system. As such, the clotting is reduced and the venous pressure (e.g., the venous pressure 632 in FIG. 6) decreases, but the blood volume (e.g., the blood volume 622 in FIG. 6) may increase. The blood pressure (e.g., the blood pressure 660 in FIG. 6) may also increase slightly and now there is more fluid to remove in order to achieve the estimated dry weight goal.

Figure 5A:
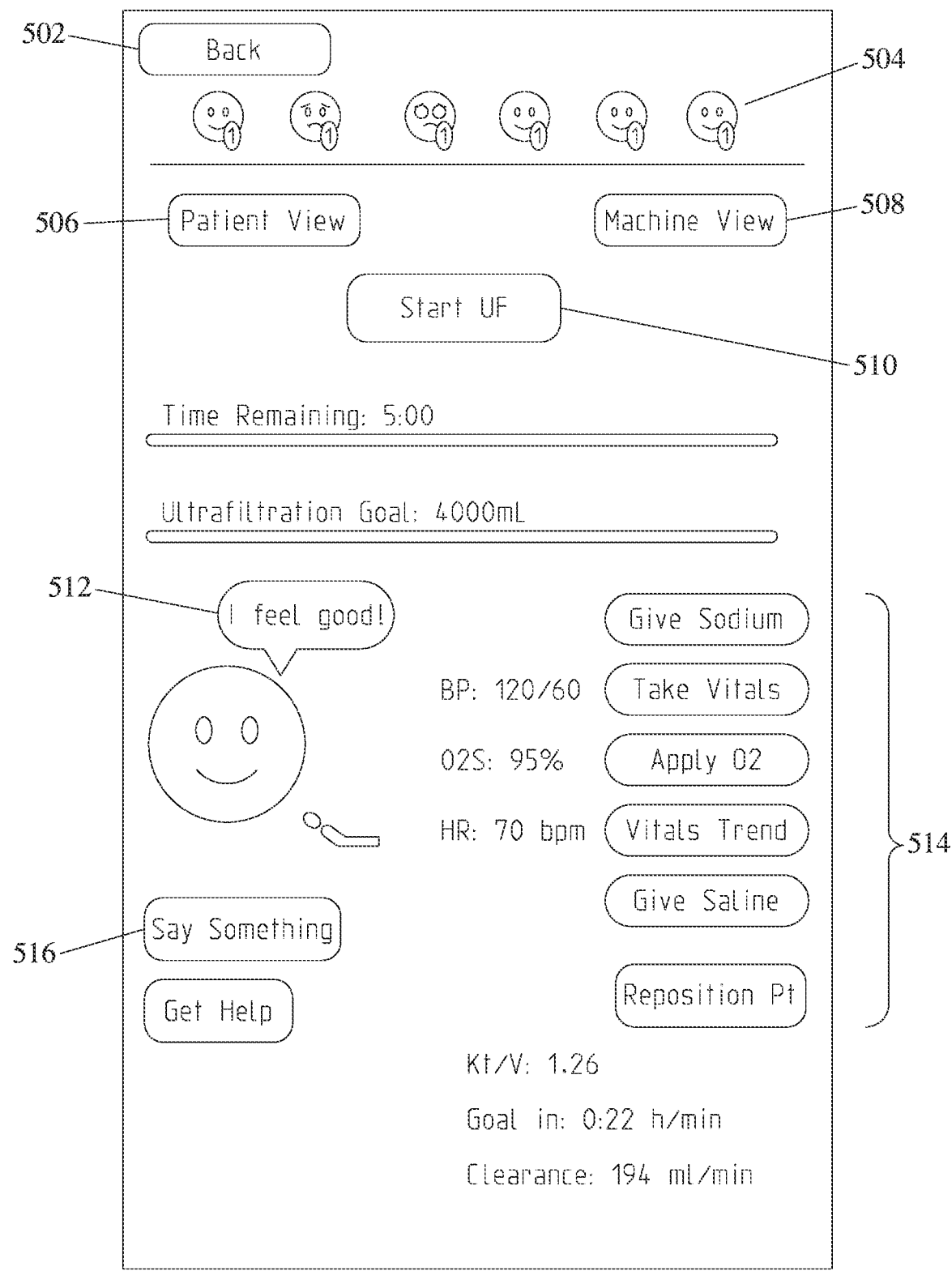
FIGS. 5A and 5B are exemplary user interfaces displayed on a user device according to one or more examples of the present application.
Figure 5B:
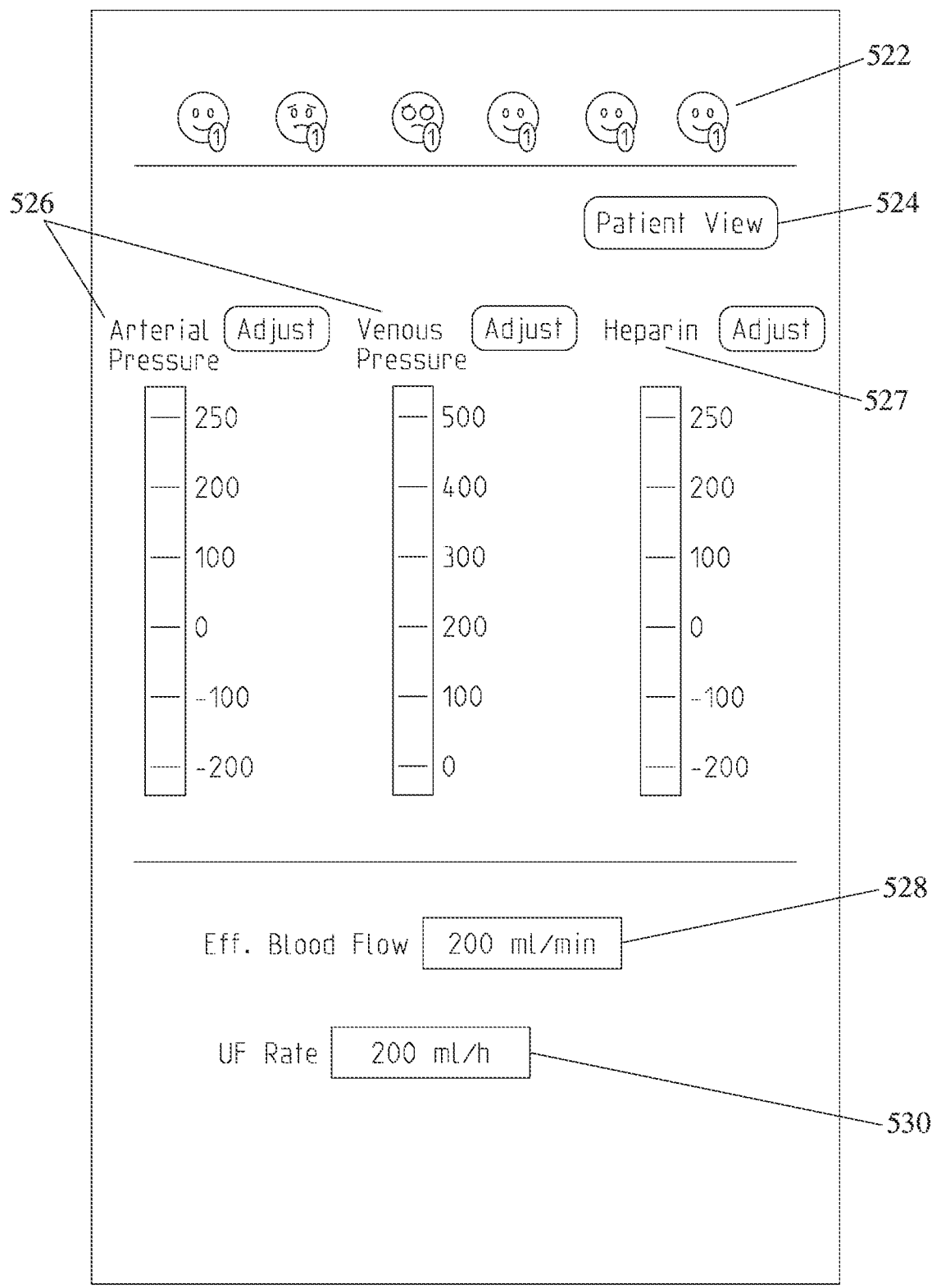

FIGS. 5A and 5B are exemplary user interfaces displayed on a user device according to one or more examples of the present application, and will be used to describe block 412 in more detail. For instance, FIG. 5A shows a user interface 500 that includes a plurality of indicia such as buttons, icons, or other information for the user 102. For instance, the indicia 502 is a back button. When selected, the user device 104 brings the user 102 back to the main menu (e.g., display a new user interface indicating the main menu). The indicia 504 are a plurality of faces showing the different patients the user is currently treating as well as the health of the patients. As such, there are six patients, with some patients doing well (smiley face indicia) and others not so well. The different faces may be based on a health variable for the patient. For instance, the user device 104 may calculate a health variable based on the patient parameters (e.g., the blood pressure of the patient) at each iteration of process 400, and display a face associated with the health. For instance, based on the health variable being 60 or above, the user device 104 may display a happy face. Based on the health variable being between 40-60, the user device 104 may display a different face such as a sad face. Then, based on the health variable being below 40, the user device 104 may display yet another face such as a sick face, and so on.

The indicia 506 is a patient view button that when selected, the user device 104 displays the current user interface (e.g., user interface 500). The indicia 508 is a machine view button that when selected, the user device 104 displays a machine user interface such as the user interface 520 shown in FIG. 5B. The indicia 510 is a start UF button that when selected, begins dialysis treatment for the patient. Below the indicia 510 include two status bars and text indicating the amount of time remaining for the dialysis treatment (5:00 minutes) as well as the ultrafiltration goal (4,000 milliliters (ml)). The indicia 512 is a patient indicia that shows the current patient's mood and comments ("I feel good"). The indicia 512 may further be associated with the health variable of the patient. The indicia 512 also shows the patient's reclining position. The indicia 514 includes a plurality of buttons associated with patient parameters. For instance, the "Take Vitals" button takes the patients vitals. The "Apply O2" button administers oxygen to the patient. The "Vitals Trend" button shows the patient's vitals history. The "Give Saline" button administers saline to the patient. The "Reposition Pt" button changes the patient's body position. The "Give Sodium" button administers sodium to the patient. One or more of the buttons of indicia 514 may be associated with a patient parameter. For instance, the apply O2 button may apply oxygen to the patient, which is shown by the oxygen given patient parameter 608 in FIG. 6. These patient parameters that may be adjusted by the user 102 using indicia 514 may have further impacts on other patient parameters (e.g., the oxygen given parameter 608 may impact the respiration parameter 606). The indicia 516 also includes two buttons. The "Say Something" button allows the user 102 to speak to the patient. The "Get Help" button allows the user to ask for assistance or notify appropriate staff in case of an emergency. Additionally, user interface 500 also shows a plurality of patient parameters such as the blood pressure ("BP"), the oxygen saturation ("O2S"), the heart rate ("HR"), and other information for the patient.

FIG. 5B shows the user interface 520, which may be shown in response to the user selecting indicia 508 from the user interface 500. Referring to the user interface 520, the indicia 522 show the different patients the user is treating, which is similar to indicia 504. Indicia 524 shows the patient view button, which causes the user device 104 to display the user interface 500. The indicia 526 shows the arterial and venous pressure adjustment, which includes an adjustment button and a numerical scale below the button, which allows the user 102 to adjust the arterial and venous pressures to a certain value. The indicia 527 shows the heparin adjustment, which includes an adjustment button and a numerical scale to allow the user 102 to adjust the heparin to a certain value. The indicia 528 allows the user 102 to change the blood pump speed and the indicia 530 allows the user 102 to change the ultrafiltration rate. The indicia 526, 527, 528, and/or 530 may be associated with the patient parameters shown in FIG. 6, which will be described below. The user interfaces and indicia/buttons shown in FIGS. 5A and 5B are exemplary and process 400 may use additional and/or alternative user interfaces for simulating the dialysis treatment.

At block 414, the user device 104 updates the patient parameters based on the received user input. For instance, referring back to FIG. 5A, the user 102 may select one of the indicia 514 such as "Give Saline" or "Apply O2". The user device 104 may receive the user input associated with the selection and update the patient parameters accordingly. Based on selecting "Give Saline", the user device 104 may increase the saline patient parameter. Based on selecting the "Apply O2", the user device 104 may increase the oxygen given patient parameter. Referring to FIG. 5B, the user 102 may further input a numerical value for one or more patient parameters. For instance, the user 102 may provide user input for a UFR using the indicia 530 or adjust the arterial pressure to a certain value using the indicia 526. Based on the user input, the user device 104 may set the patient parameter to the user provided value.

At block 416, the user device 104 updates additional patient parameters, the health of the patient, and/or dialysis event variables. For instance, the patient parameters may be interconnected and/or related to each other such that by changing one patient parameter, the user device 104 may further change one or more additional patient parameters for the patient. The user device 104 may update the additional patient parameters based on the user input from block 414, based on the initiated dialysis event, and/or based on the continuation of the dialysis treatment. For instance, as mentioned above, by initiating a dialysis event, the user device 104 may update the patient parameters associated with the event. For example, based on initiating a high UFR event, the user device 104 may update the blood volume parameter and the arterial pressure by decreasing both of these patient parameters. The user device 104 may further increase the pulse and demand for oxygen patient parameters as well as decrease the patient's level of consciousness. Additionally, and/or alternatively, by initiating a clotting event, the user device 104 may increase the dialyzer resistance patient parameter and increase the venous pressure.

Furthermore, the user device 104 may update additional patient parameters based on the user input. For example, patient parameters may be interconnected to each other such that changing one patient parameter also changes one or more additional patient parameters. For example, the user input may indicate to apply oxygen or provide a new value for the UFR. The apply oxygen patient parameter and the UFR patient parameter may be related to one or more additional patient parameters. For instance, the apply oxygen patient parameter may be related to the respiration patient parameter, which may further be related to the oxygen saturation patient parameter. Similarly, the UFR patient parameter may be related to the fluid removal patient parameter, which may be related to the blood volume patient parameter. As such, at block 414, the user device 104 may update the patient parameter associated with the user input (e.g., the apply oxygen patient parameter and/or the UFR patient parameter). At block 416, the user device 104 may update one or more additional patient parameters that are associated with the patient parameter of block 414. For instance, the user device 104 may update the oxygen saturation patient parameter and/or the fluid removal patient parameter based on the user input indicating to apply oxygen to the patient.

FIG. 6 is a graphical representation of exemplary interconnectivity and relationships between the patient parameters according to one or more examples of the present application. For instance, the user device 104 may use the graphical representation 600 to update the additional patient parameters at block 416. Each block within the graphical representation 600 is associated with a single patient parameter. The patient parameters may separated into two groups—user adjustable patient parameters (e.g., the user can provide user input to directly control the patient parameter) or a patient parameter that is not user adjustable (e.g., the user might not be able to directly influence these patient parameters using user input as they are part of the patient's physiology, but can adjust other patient parameters that will impact these patient parameters). The dotted boxes (e.g., oxygen given 608) denote user adjustable patient parameters and the straight-line boxes (e.g., oxygen demand 604) denote patient parameters that are not user adjustable. In some instances, while one or more patient parameters may be denoted as user adjustable or not user adjustable, the patient parameters may be both user adjustable and not user adjustable (e.g., the dialyzer resistance 630, arterial pressure 612, and venous pressure 632 may be user adjustable in some embodiments and not user adjustable in other embodiments).

Additionally, the patient parameters may have different relationships with other patient parameters. The "−" icon indicates an indirect relationship (e.g., when the first patient parameter increases, the related parameter decreases), the "+" icon indicates a direct relationship (e.g., when the first patient parameter increases, the related parameter also increases), the "*" icon indicates an aggregation relationship (e.g., two or more patient parameters may impact their related patient parameter), and the "Δ" indicates a variation of rate on a variable (e.g., a non-linear relationship between the first parameter and the related parameter).

For example, the level of consciousness 602 (e.g., a patient parameter indicating how conscious the patient is including whether the patient is unconscious), the oxygen demand 604 (e.g., the oxygen demand of the patient), the respiration 606 (e.g., the patient's respiration rate), the oxygen saturation 616 (e.g., the patient's oxygen saturation), the pulse 610 (e.g., the patient's pulse), and the blood pressure 660 (e.g., the blood pressure (BP) of the patient) may be patient parameters that the user 102 cannot directly adjust. However, as shown in FIG. 5A, indicia 514 includes an "Apply O2" button. When the user 102 selects this button, the oxygen given 608 may increase. Then, as shown, the oxygen given 608 may have an indirect relationship (e.g., "−") with the respiration patient parameter 606 such that when the oxygen given 608 increases, the respiration 606 decreases. The respiration 606 may have a direct relationship (e.g., "+") with the oxygen saturation 616 such that the oxygen saturation 616 increases when the respiration 606 increases. The oxygen demand 604 may have a direct relationship with an aggregation of the BP 660 and the oxygen saturation 616. For example, the oxygen saturation 616 and the BP 660 may be aggregated together (e.g., "*"), and the aggregation may have an indirect relationship (e.g., "−") with the oxygen demand 604. In other words, when both BP 660 and oxygen saturation 616 increases, the demand for oxygen decreases. The oxygen demand 604 may have an indirect relationship with the level of consciousness 602 (e.g., as the demand for oxygen increases, the level of consciousness decreases as the patient's body recognizes that it needs more oxygen), a direct relationship with the respiration 606, and a direct relationship with the pulse 610 (e.g., as the demand for oxygen increases, the pulse increases in an attempt to circulate more oxygen). The pulse 610 may have a direct relationship with the BP 660.

In some instances, a patient parameter (e.g., the respiration 606) may have two or more relationships with other patient parameters. During each iteration of process 400 or for each user input, the patient parameter may only be adjusted a set number of times (e.g., one or two times). For instance, the oxygen given 608 may increase, which decreases the respiration 606. The respiration 606 may impact the oxygen saturation 616 and the oxygen demand 604. The oxygen demand 604 may then influence the respiration 606 again. However, since the respiration 606 has already been altered by the oxygen given 608, the respiration 606 might not be altered again by the oxygen given 608.

The position 620 (e.g., indicating a position of the patient) may be a user adjustable parameter that may be adjusted by the "Reposition Pt" button of indicia 514. For example, the patient may be repositioned to be upright, lying down, and so on. The position 620 may have an indirect relationship with the BP rate of change ("BP-cr") 618, which may have a variable relationship (e.g., "Δ") with the BP 660. The BP rate of change 618 and the BP 660 may be patient physiology parameters. For instance, the BP rate of change 618 may have a variable relationship with the BP 660 such that the BP 660 may be adjusted more quickly based on the BP rate of change 618.

The venous pressure 632 may have a direct relationship with the dialyzer resistance 630. The arterial pressure 612 may have an indirect relationship with the BP 660. The venous pressure 632 and the arterial pressure 612 may indicate problems for the patient such as clotting, misplaced needles, and so on. The dialyzer resistance 630 may be a reduction in the volume of blood going through the dialyzer because of an obstruction such as clotting, which may impact the venous pressure 632.

The heparin 646 may be a user adjustable parameter and indicate the amount of heparin provided to the patient. For instance, referring to FIG. 5B, the user 102 may use the indicia 527 to adjust the heparin provided for the patient. The heparin 646 may have an indirect relationship with the clotting parameter 638. The clotting parameter 638 may be a physiology parameter that is not user adjustable. The clotting parameter 638 may have a direct relationship with the dialyzer resistance 630. The dialyzer resistance 630 may be a machine parameter that may be user adjustable or may be a machine variable that is not user adjustable. The dialyzer resistance 630, in addition to having a direct relationship with the venous pressure, may further have a direct relationship with the pump speed 614 and an indirect relationship with the fluid given 628. For example, referring to FIG. 5B, the pump speed 614 may be a user adjustable parameter that is adjustment using the indicia 528. Based on the user input, the pump speed 614 may be increased or decreased, which may impact the dialyzer resistance 630 as well as the BP 660 (e.g., via an indirect relationship). Further, referring to FIG. 5A, the "Give Saline" button for indicia 514 may cause an increase to the fluid given parameter 628. The fluid given parameter 628 may have an indirect relationship with the dialyzer resistance 630 and a direct relationship to the blood volume 622 (e.g., the blood volume of the patient). The blood volume 622 may be a physiological parameter that is not user adjustable.

The give sodium ("Give Na++") patient parameter 644 may be user adjustable. For instance, referring to FIG. 5A, the "Give Sodium" button for indicia 514 may cause an increase to the give sodium parameter 644. The give sodium parameter 644 may have a direct relationship with the refill rate 636 (e.g., a refill rate may be the amount of time it takes the body to compensate for the fluid removed from the bloodstream by drawing from other areas of the body). The refill rate 636 may be a physiological parameter that is not user adjustable. The refill rate 636 and the UFR 634 may be aggregated and have a direct relationship with the blood volume 622.

The patient weight incoming ("Pt Wt In") 650 and the estimated dry weight (EDW) 648 may be aggregated and have a direct relationship with the ultrafiltration (UF) goal 642. The patient weight incoming 650 is the weight of the patient at the beginning of the dialysis treatment. The EDW 648 is the estimated weight of the patient without the excess fluid within the patient's body. The EDW 648 for the patient may be within the history note. For instance, the patient parameters 648, 650, and/or 642 may be patient specific (e.g., based on the height, weight, and/or other characteristics of the patient) and may be retrieved by the user device 104 when starting the dialysis treatment. The treatment time ("Tx Time") 640 may be a machine variable and a timer that indicates the amount of time allotted for the dialysis treatment for the patient. The UF goal 642 and the treatment time 640 may be displayed on the user interface such as shown in FIG. 5A. The UF goal 642 and the treatment time 640 may be aggregated and have a direct relationship with the UFR 634. For example, initially, the UFR 634 may be set based on the UF goal 642 and the treatment time 640. Then, during the dialysis treatment, the UFR 634 may be changed by the user 102 using the indicia 630 of FIG. 5B. The UFR 634 and the refill rate 636 may be aggregated and have a direct relationship with the blood volume 622. The UFR 634 may further have a direct relationship with the fluid removal 624 (e.g., the amount of fluid removed by the dialysis treatment currently). The access flow 626 and the fluid removal 624 may be aggregated and have an indirect relationship with the blood volume 622. The access flow 626 may be a physiological parameter that is not adjustable by the user. The access flow 626 may indicate the rate at which a volume of fluid may pass through an access over a given period of time. For instance, if fluid is pulled from an access faster than it can handle, then pressure issues may arise or other issues that may cause the dialysis machine to stop. The blood volume 622 may have a direct relationship with the blood pressure.

The graphical representation 600 showing the inter-connectivity between the patient parameters is merely exemplary and the user device 104 may use additional or alternative relationships between the patient parameters to update the additional patient parameters in block 416.

Furthermore, at block 416, the user device 104 may update the health of the patient. For instance, based on the updated blood pressure (e.g., BP 660) and/or the level of consciousness 602, the user device 104 may determine a health of the patient. Additionally, and/or alternatively, the user device 104 may use other patient parameters to determine the health of the patient including, but not limited to, the pulse 610, the respiration 606, O2 saturation 616, and/or patient complaints. In some instances, the health of the patient may be a value between 0-100. Based on the level of consciousness indicating the patient is conscious and the blood pressure being within a normal range, the user device 104 may determine a high health value (e.g., 90 to 100). But, if the level of consciousness indicates the patient is unconscious and/or the blood pressure is abnormal, the user device 104 may determine a lower health value. The user device 104 may use an algorithm or other process to determine the health of the patient. Then, using the health of the patient, the user device 104 may determine and display a smiley face (e.g., the smiley face indicia 504 shown in FIG. 5A) or another prompt indicating the health of the patient. In some instances, if the health of the patient is too low (e.g., the blood pressure of the patient is below a critical amount or the patient has been unconscious for a sufficient amount of time), the user device 104 may determine the virtual patient has died and provide a prompt indicating that the virtual patient has died.

The user device 104 may further update one or more dialysis event variables. For instance, after initiating a dialysis event at block 410, the user device 104 may lower the dialysis event variable associated with the dialysis event so that the dialysis event does not occur in the next iteration. Additionally, and/or alternatively, the user device 104 may increase one or more dialysis event variables based on the dialysis event not occurring yet during the simulated dialysis treatment.

At block 418, the user device 104 determines whether the time step counter reaches the time threshold. For instance, referring to FIG. 5A and as described above, each level may be a certain length of time (e.g., 5:00 minutes remaining). Further, each time step may be a certain length of time (e.g., 5 seconds). At block 418, the user device 104 checks whether the time step counter has reached the allowed time for the level (e.g., 5 minutes). If so, process 400 moves to block 420. Otherwise, process 400 moves to block 406 and repeats.

In other words, using process 400, the application continuously updates patient parameters throughout blocks 406-418 so as to simulate one or more dialysis patients undergoing dialysis treatment. The user 102 may provide user input (e.g., by selecting indicia 514, 516, and/or others) to adjust one or more patient parameters. The patient parameters that the user 102 can adjust have relationships with other patient parameters (as shown in FIG. 6) and the user interface continuously updates the patient parameters accordingly. Furthermore, the application may provide dialysis events (e.g., a needle has come loose or the patient is wanting to get taken off dialysis) based on using the dialysis event variables. The dialysis events may provide a prompt and request user feedback. For instance, the event may indicate for the user 102 to select the indicia 516 for saying something or getting help. Additionally, and/or alternatively, the event may indicate for the user 102 to adjust certain patient parameters to ensure the patient is properly being handled. For instance, the event may indicate the patient is unconscious and for the user 102 to adjust patient parameters to ensure the patient is safe.

Because each patient has their own patient parameters and dialysis event variables, as more patients come under the user's 102 care, it becomes harder for the user 102 to manage these patients. As such, each level may progressively get harder for the user 102 in the dialysis simulation.

At block 420, the user device 104 determines and outputs a score for the completed level. The user device 104 may use the patient parameters throughout the dialysis treatment to determine the score. For instance, based on the patients under the user's 102 care being conscious, the patient being within a normal blood pressure range over a period of time, removing enough fluid within the patient to get the patient to their estimated dry weight (EDW), keeping the patient on the dialysis treatment for the duration of the prescribed treatment length, getting the patients on/off their dialysis treatments on time, having the blood volume of the patient being within a certain threshold, and/or additional or alternative goals, the user device 104 may calculate and output a score. Based on the score, the user device 104 may determine whether to unlock the next level for the user 102. For instance, based on the user 102 keeping the patient's alive and/or reaching the patient's EDW within an allotted time, the user device 104 may determine to unlock the next level for the user 102. The user device 104 may use any type of algorithm or method to determine the score and determine whether to unlock the next level for the user 102.

Additionally, and/or alternatively, the user device 104 may provide a prompt indicating one or more outcomes for the patient and the reasons behind the outcome so as to provide a lesson for the user 102. For instance, the user device 104 may provide a prompt indicating the fluid goal might not have been achieved due to excessive breaks that were used to compensate for the low blood pressure. The user device 104 may provide a prompt indicating that too much fluid was removed or the ultrafiltration rate was not well tolerated at a high enough rate to achieve the goal. The user device 104 may provide a prompt indicating the patient lost consciousness at one or more times during the dialysis treatment because of uncontrolled blood pressure, causing reduction on oxygen to the brain. The user device 104 may provide a prompt indicating the patient was removed early from the dialysis treatment because of physical discomfort or loss of patience. The user device 104 may provide a prompt indicating one or more patients started or stopped off-schedule, causing disruption in subsequent shifts.

Figure 7:
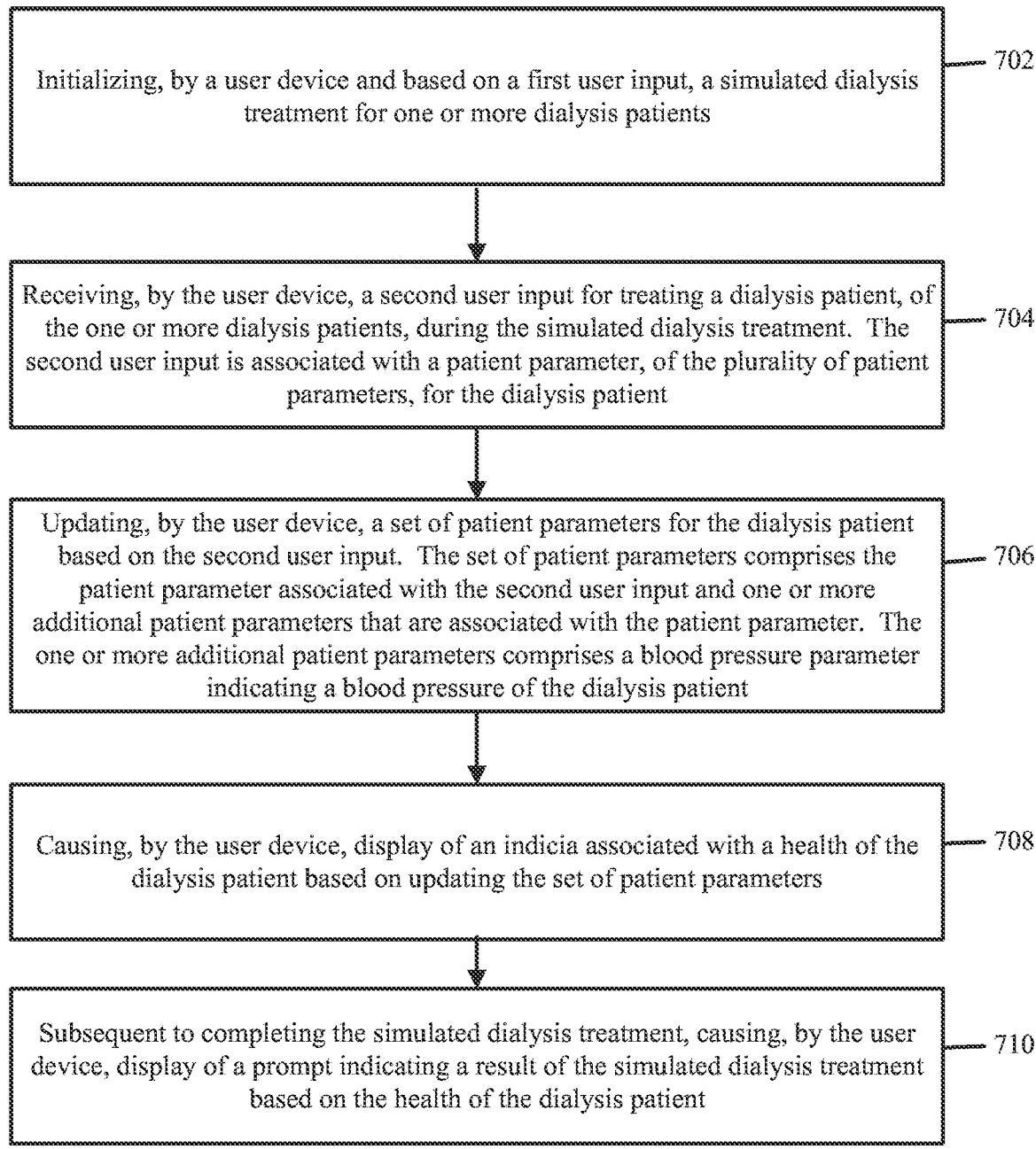
FIG. 7 is another flowchart of another exemplary process for training an operator by simulating dialysis treatments according to one or more examples of the present application.

FIG. 7 is another flowchart of another exemplary process for training an operator by simulating dialysis treatments according to one or more examples of the present application. The process may be performed by a user device such as the user device 104 depicted in FIG. 2. However, it will be recognized that any of the following blocks may be performed in any suitable order, and that the process 700 may be performed in any suitable environment. The descriptions, illustrations, and processes of FIG. 7 are merely exemplary and the process 700 may use other descriptions, illustrations, and processes for providing dialysis treatment training.

At block 702, the user device 104 initializes, based on first user input, a simulated dialysis treatment for one or more dialysis patients. At block 704, the user device 104 receives a second user input for treating a dialysis patient, of the one or more dialysis patients, during the simulated dialysis treatment. The second user input is associated with a patient parameter, of a plurality of patient parameters, for the dialysis patient. At block 706, the user device 104 updates a set of patient parameters, of the plurality of patient parameters, for the dialysis patient based on the second user input. The set of patient parameters comprises the patient parameter associated with the second user input and one or more additional patient parameters that are associated with the patient parameter. The one or more additional patient parameters comprises a blood pressure parameter indicating a blood pressure of the dialysis patient. At block 708, the user device 104 causes display of an indicia associated with a health of the dialysis patient based on updating the set of patient parameters. At block 710, subsequent to completing the simulated dialysis treatment, the user device 104 causes display of a prompt indicating a result of the simulated dialysis treatment based on the health of the dialysis patient.

In some instances, the application may be a mobile application and the user device 104 may be a mobile phone (e.g., smart phone). For instance, by having the application being a mobile application operated on a mobile phone, the application may be highly accessible for short session use, may be in a medium that most users have personal access to almost anywhere, and/or may keep it simple and available when users only have a few minutes for a simulation of a level.

In some examples, the user device 104 may use VR or AR to train the user 102 in performing dialysis treatment. For instance, the user device 104 may display an AR or VR environment with a dialysis machine, and the user 102 may move around the AR or VR environment and perform a simulated dialysis treatment on the patient. In other words, rather than displaying buttons and/or adjustment settings on a graphical user interface such as the interfaces shown in FIGS. 5A and 5B, the user device 104 may display a simulated dialysis machine and patient in an AR or VR environment, which may be used to train the user 102.

In some variations, an actual medical system such as the medical system 110 shown in FIGS. 1 and 2 may be used to perform training of the user 102. For instance, the medical system 110 may be a hemodialysis machine as shown in FIG. 1 and may include a display that displays information to the user 102. The medical system 110 may perform process 400 described above such as determine whether to perform dialysis events, receive user inputs, update patient parameters (e.g., the patient parameters associated with the user input and/or additional patient parameters related to the patient parameters associated with the user input, which is described in FIG. 6 above) as well as health variables of the patient and/or dialysis event variables, and/or determine and output a score for the training. In such variations, rather than the user 102 inputting all their user input on a graphical user interface, the user 102 may provide user input directly to the hemodialysis machine. For example, instead of adjusting the UF rate on a graphical user interface of a mobile device, the user 102 may provide user input on the actual hemodialysis machine to adjust the UF rate. The hemodialysis machine may include a user input interface that is used to provide information to the processors of the hemodialysis machine. For instance, the processors may receive information indicating a change of the UF rate or the user 102 providing saline or sodium to the patient. Based on the received information, the processors may update the patient parameters such as the patient parameters for the UFR 634, the give sodium parameter 644, and/or the fluid given parameter 628 shown in FIG. 6. Furthermore, the processors may update additional patient parameters and/or determine the health of the patient as described above.

In some instances, the principles discussed herein (e.g., the dialysis simulation) may be applicable to hemodialysis systems. In other instances, the principles discussed herein may be applicable to other types of dialysis systems, such as systems for peritoneal dialysis in which a patient's peritoneal cavity is periodically infused with dialysate, and for which the membranous lining of the patient's peritoneum acts as a natural semi-permeable membrane that allows diffusion and osmosis exchanges to take place between the solution and the blood stream.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A hemodialysis system, comprising:
a hemodialysis machine having an extracorporeal blood circuit with a blood chamber and a dialyzer, wherein the hemodialysis machine is configured to perform a hemodialysis treatment for a patient; and
an optical monitoring system, comprising a sensor device configured to emit light through the blood chamber and measure optical characteristics of extracorporeal blood in the blood chamber,
wherein the hemodialysis machine includes or is connected to a user input interface, a display, and one or more processors configured to:
receive, via the user input interface, a first user input indicating to initialize a simulated dialysis treatment for a simulated dialysis patient;
determine a plurality of dialysis event variables associated with a plurality of dialysis events based on the first user input;
execute one or more dialysis events of the plurality of dialysis events based on comparing one or more results from a random number generator with one or more dialysis event variables of the plurality of dialysis event variables;
in response to executing the one or more dialysis events, receive, via the user input interface, a second user input for treating the simulated dialysis patient during the simulated dialysis treatment, wherein the second user input indicates an adjustment of a first adjustable patient parameter from a plurality of patient parameters, wherein the plurality of patient parameters comprises a plurality of adjustable patient parameters including the first adjustable patient parameter and a plurality of non-adjustable patient parameters;
update a set of patient parameters of the plurality of patient parameters for the simulated dialysis patient based on the second user input and executing the one or more dialysis events, wherein updating the set of patient parameters comprises:
updating the first adjustable patient parameter based on the second user input;
determining one or more non-adjustable patient parameters plurality of non-adjustable patient parameters that have one or more relationships to the first adjustable patient parameter, wherein the one or more non-adjustable patient parameters comprises a blood pressure parameter indicating a blood pressure of the simulated dialysis patient; and
updating the one or more non-adjustable patient parameters based on updating the first adjustable patient parameter and the one or more relationships to the first adjustable patient parameter;
display indicia on the display, wherein the indicia is associated with a health of the simulated dialysis patient based on updating the set of patient parameters; and
subsequent to completing the simulated dialysis treatment, display a prompt on the display indicating a result of the simulated dialysis treatment based on the health of the simulated dialysis patient.

2. The hemodialysis system of claim 1, wherein the one or more processors are further configured to:
receive, from the one or more sensors, a third user input for treating the simulated dialysis patient during the simulated dialysis treatment, wherein the third user input is associated with a second adjustable patient parameter, of the plurality of patient parameters, for the simulated dialysis patient, wherein the second adjustable patient parameter is different from the first adjustable patient parameter; and
update a second set of patient parameters of the plurality of patient parameters for the simulated dialysis patient based on the third user input, wherein the second set of patient parameters comprises the second adjustable patient parameter associated with the third user input, the blood pressure parameter, and a third patient parameter that is associated with the second adjustable patient parameter.

3. The hemodialysis system of claim 1, wherein the one or more relationships between the first adjustable patient parameter and the one or more non-adjustable patient parameters is a direct relationship or an indirect relationship.

4. A computing device, comprising:
a user input interface;
a display configured to display information associated with a simulated dialysis treatment; and
one or more processors configured to:
receive, from the user input interface, a first user input indicating to initialize the simulated dialysis treatment for a simulated dialysis patient;
determine a plurality of dialysis event variables associated with a plurality of dialysis events based on the first user input;
execute one or more dialysis events of the plurality of dialysis events based on comparing one or more results from a random number generator with one or more dialysis event variables of the plurality of dialysis event variables;

in response to executing the one or more dialysis events, receive, from the user input interface, a second user input for treating the simulated dialysis patient during the simulated dialysis treatment, wherein the second user input indicates an adjustment of a first adjustable patient parameter from a plurality of patient parameters, wherein the plurality of patient parameters comprises a plurality of adjustable patient parameters including the first adjustable patient parameter and a plurality of non-adjustable patient parameters;

update a set of patient parameters of the plurality of patient parameters for the simulated dialysis patient based on the second user input and executing the one or more dialysis events, wherein updating the set of patient parameters comprises:

updating the first adjustable patient parameter based on the second user input;

determining one or more non-adjustable patient parameters plurality of non-adjustable patient parameters that have one or more relationships to the first adjustable patient parameter; and updating the one or more non-adjustable patient parameters based on updating the first adjustable patient parameter and the one or more relationships to the first adjustable patient parameter;

display indicia on the display, wherein the indicia is associated with a health of the simulated dialysis patient based on updating the set of patient parameters; and subsequent to completing the simulated dialysis treatment, display a prompt on the display indicating a result of the simulated dialysis treatment based on the health of the simulated dialysis patient.

5. The computing device of claim 4, wherein the one or more processors are further configured to:

receive, from the user input interface, a third user input for treating the simulated dialysis patient during the simulated dialysis treatment, wherein the third user input is associated with a second adjustable patient parameter, of the plurality of patient parameters, for the simulated dialysis patient, wherein the second adjustable patient parameter is different from the first adjustable patient parameter; and update a second set of patient parameters of the plurality of patient parameters for the simulated dialysis patient based on the third user input, wherein the second set of patient parameters comprises the second adjustable patient parameter associated with the third user input, a blood pressure parameter, and a third patient parameter that is associated with the second adjustable patient parameter.

6. The computing device of claim 4, wherein the one or more relationships between the first adjustable patient parameter and the one or more non-adjustable patient parameters is a direct relationship or an indirect relationship.

7. A method, comprising:

receiving, from a user input interface of a mobile device, a first user input indicating to initialize a simulated dialysis treatment for one or more dialysis patients, wherein the mobile device comprises the user input interface and a display;

determining, by the mobile device, a plurality of dialysis event variables associated with a plurality of dialysis events based on the first user input;

executing, by the mobile device, one or more dialysis events of the plurality of dialysis events based on comparing one or more results from a random number generator with one or more dialysis event variables of the plurality of dialysis event variables;

in response to executing the one or more dialysis events, receiving, from the user input interface of the mobile device, a second user input for treating a dialysis patient, of the one or more dialysis patients, during the simulated dialysis treatment, wherein the second user input indicates an adjustment of a first adjustable patient parameter from a plurality of patient parameters, wherein the plurality of patient parameters comprises a plurality of adjustable patient parameters including the first adjustable patient parameter and a plurality of non-adjustable patient parameters;

updating, by the mobile device, a set of patient parameters of the plurality of patient parameters for the dialysis patient based on the second user input and executing the one or more dialysis events, wherein updating the set of patient parameters comprises:

updating the first adjustable patient parameter based on the second user input;

determining one or more non-adjustable patient parameters from plurality of non-adjustable patient parameters that have one or more relationships to the first adjustable patient parameter; and updating the one or more non-adjustable patient parameters based on updating the first adjustable patient parameter and the one or more relationships to the first adjustable patient parameter;

displaying, by the display of the mobile device, indicia associated with a health of the dialysis patient based on updating the set of patient parameters; and subsequent to completing the simulated dialysis treatment, displaying, by the display of the mobile device, a prompt indicating a result of the simulated dialysis treatment based on the health of the dialysis patient.

8. The method of claim 7, further comprising:

receiving, from the user input interface of the mobile device, a third user input for treating the dialysis patient during the simulated dialysis treatment, wherein the third user input is associated with a second adjustable patient parameter, of the plurality of patient parameters, for the dialysis patient, wherein the second adjustable patient parameter is different from the first adjustable patient parameter; and updating, by the mobile device, a second set of patient parameters of the plurality of patient parameters for the dialysis patient based on the third user input, wherein the second set of patient parameters comprises the second adjustable patient parameter associated with the third user input, a blood pressure parameter, and a third patient parameter that is associated with the second adjustable patient parameter.

9. The method of claim 7, wherein the first adjustable patient parameter and a blood pressure parameter have a relationship with the one or more non-adjustable patient parameters.

10. The method of claim 7, wherein the one or more relationships between the first adjustable patient parameter and the one or more non-adjustable patient parameters is a direct relationship.

11. The method of claim 7, wherein the one or more relationships between the first adjustable patient parameter and the one or more non-adjustable patient parameters is an indirect relationship.

12. The method of claim 7, further comprising:
during the simulated dialysis treatment, displaying, by the display of the mobile device, a graphical user interface comprising a plurality of indicia, wherein the plurality of indicia comprises the indicia associated with the health of the dialysis patient and a user-selectable indicia that adjusts the first adjustable patient parameter, wherein receiving the second user input is based on a user selecting the user-selectable indicia.

13. The method of claim 12, wherein the first adjustable patient parameter and the user-selectable indicia are associated with an ultrafiltration rate for the dialysis patient or a heparin amount provided to the dialysis patient.

14. The method of claim 12, wherein the first adjustable patient parameter and the user-selectable indicia are associated with adjusting a position of the dialysis patient or an amount of oxygen given to the dialysis patient.

15. The method of claim 7, wherein the one or more dialysis events comprises a clotting event indicating the dialysis patient has a clot.

16. The method of claim 7, further comprising:
updating one or more of the plurality of dialysis event variables based on executing the one or more dialysis events.

17. The method of claim 7, wherein the plurality of patient parameters comprises a blood pressure parameter and a consciousness parameter of the dialysis patient, wherein the method further comprises:
determining the health of the dialysis patient based on the blood pressure parameter and the consciousness parameter.

18. The method of claim 17, wherein determining the health of the dialysis patient comprises determining whether the consciousness parameter indicates the dialysis patient is conscious and the blood pressure parameter being within a blood pressure threshold.

19. The method of claim 7, wherein the first adjustable patient parameter is an oxygen given patient parameter, and wherein the one or more non-adjustable patient parameters comprises a respiration patient parameter and an oxygen saturation patient parameter.

* * * * *